United States Patent [19]

Liechti et al.

[11] Patent Number: 5,116,958
[45] Date of Patent: May 26, 1992

[54] DISPERSE DYES WHICH ARE CONVERTIBLE INTO A THERMOMIGRATION FAST FORM

[75] Inventors: Peter Liechti, Arisdorf; Martin Trottmann, Therwil, both of Switzerland

[73] Assignee: Ciba-Geigy Corporation, Ardsley, N.Y.

[21] Appl. No.: 461,497

[22] Filed: Jan. 5, 1990

[30] Foreign Application Priority Data

Jan. 13, 1989 [CH] Switzerland .................... 107/89

[51] Int. Cl.$^5$ ............... C09B 23/14; C09B 29/08; D06P 1/16
[52] U.S. Cl. .................... 534/591; 534/732; 534/733; 534/774; 534/778; 534/788; 534/794; 534/852; 534/854; 540/450; 540/524; 540/529; 546/200; 546/204; 546/221; 548/253; 548/426; 552/223; 558/403
[58] Field of Search ............... 534/591, 774, 778, 788, 534/794, 852, 854, 732, 733; 540/450, 524, 529; 546/200, 204, 221; 548/253, 426; 552/223; 564/155, 196; 558/403

[56] References Cited

U.S. PATENT DOCUMENTS

| | | | |
|---|---|---|---|
| 4,006,163 | 2/1977 | Kolliker | 548/426 |
| 4,119,621 | 10/1978 | Hansen et al. | 534/733 |
| 4,914,190 | 4/1990 | Liechti | 534/859 |

FOREIGN PATENT DOCUMENTS

| | | | |
|---|---|---|---|
| 2752805 | 5/1979 | Fed. Rep. of Germany | 534/788 |
| 2108710 | 9/1970 | France | |
| 824443 | 12/1959 | United Kingdom | |
| 1351375 | 4/1974 | United Kingdom | 534/788 |
| 2024836 | 1/1980 | United Kingdom | 534/788 |
| 2028820 | 3/1980 | United Kingdom | |
| 2038849 | 7/1980 | United Kingdom | 534/733 |

OTHER PUBLICATIONS

Gheorghiu et al, *Chemical Abstracts*, vol. 52, No. 14635h (1958).

Primary Examiner—Mary C. Lee
Assistant Examiner—Fiona T. Powers
Attorney, Agent, or Firm—Marla J. Mathias; Edward McC. Roberts

[57] ABSTRACT

Disperse dyes, which produce dyeings of excellent thermomigration fastness, consisting of a chromophore and a lactam or oxime radical which detaches on heating to leave an isocyanate or isothiocyanate group, which reacts with a suitable group in the environment. The disclosed dyes are described by the formula

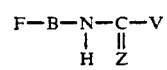 (1)

where
F is the radical of a dye which is free of water-solubilizing groups,
B is a bridge member or a direct bond,
Z is O or S and
V is the radical of a group H—V, where H—V is an oxime of the formula

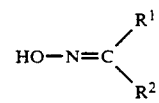 (2)

or a lactam of the formula

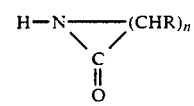 (3)

in which
R$^1$ and R$^2$ are each independently of the other substituted or unsubstituted alkyl or aryl, or
R$^1$ and R$^2$ together with the carbon atom linking them form a cycloaliphatic ring,
R is hydrogen or alkyl and
n is an integer from 4 to 11.

11 Claims, No Drawings

DISPERSE DYES WHICH ARE CONVERTIBLE INTO A THERMOMIGRATION FAST FORM

The present invention relates to novel disperse dyes, to processes for preparing same, and to processes for dyeing and printing using these dyes.

Disperse dyes, i.e. dyes which do not contain any water-solubilizing groups, are long known and are used as dyes for dyeing, for example, hydrophobic textile material. Frequently, however, the dyeings obtained are not sufficiently fast to thermomigration.

Endeavours to remedy this defect led to the development of specific dyes of minimal diffusibility as a consequence of their molecular size and/or bulkiness. These features, however, make it difficult to use these dyes, since they are very difficult, if not impossible, to dye by the exhaust method and they frequently require undesirably high fixing temperatures even in the thermosol process.

The present invention accordingly provides disperse dyes which can be applied in a conventional manner and which can be converted by a thermal aftertreatment into a form where they are fast to thermomigration.

The dyes according to the present invention conform to the formula

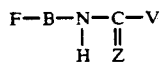  (1)

where
F is the radical of a dye which is free of water-solubilizing groups,
B is a bridge member or a direct bond,
Z is O or S and
V is the radical of a group H—V, were H—V is an oxime of the formula

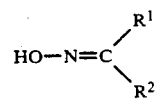  (2)

or a lactam of the formula

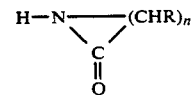  (3)

in which
R$^1$ and R$^2$ are each independently of the other substituted or unsubstituted alkyl or aryl, or
R$^1$ and R$^2$ together with the carbon atom linking them form a cycloaliphatic ring,
R is hydrogen or alkyl and
n is an integer from 4 to 11.

On being heated to elevated temperature, for example to a temperature above 110° C., the dyes according to the present invention eliminate the radical H—V, leaving isocyanate or isothiocyanate groups which can react with suitable groups in their environment, for example with the hydroxyl end groups of the polyester or an oligomer thereof or with amines of the formula F—B—NH$_2$ which can form from the isocyanates or isothiocyanates from hydration and decarboxylation and can react with a further isocyanate or isothiocyanate molecule to give compounds of the formula

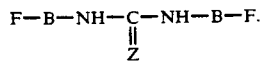

The radical F is the radical of a water-insoluble chromophore, for example the radical of one of the known disperse dyes. Possibilities are for example dye radicals of the following classes:

nitro dyes, for example nitrodiphenylamine dyes, methine dyes, quinoline dyes, aminonaphthoquinone dyes, coumarin dyes and in particular anthraquinone dyes, tricyanovinyl dyes and azo dyes, such as monoazo and disazo dyes.

The bridge member B is for example a straight-chain or branched alkylene group of 2 to 8 carbon atoms or one of the following groups:

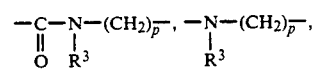

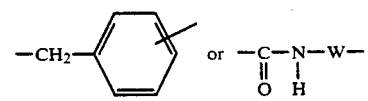

where R$^3$ is hydrogen or C$_1$-C$_6$alkyl, p is an integer from 1 to 8, and W is a divalent organic radical.

Suitable radicals W are for example: straight-chain or branched alkylene groups of 2 to 8 carbon atom, unsubstituted or C$_1$-C$_4$alkyl-substituted phenylene, C$_1$-C$_4$alkylene-phenylene-C$_1$-C$_4$alkylene, phenylene-C$_1$-C$_4$alkylene-phenylene or radicals derived from isophorone diisocyanate. Preferred radicals W are the following:

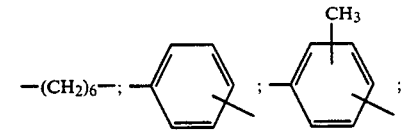

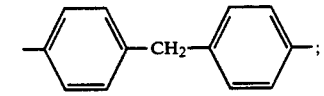

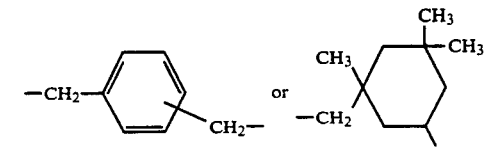

Of these bridge members, the following are particularly preferred:

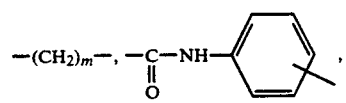

-continued

[chemical structures showing various —C(=O)—N(H)— groups attached to substituted phenyl, cyclohexyl, and biphenyl radicals]

where
m is an integer from 2 to 6.
Z is O or S, preferably O.
$R^1$ and $R^2$ are each independently of the other alkyl, preferably $C_1$-$C_{12}$alkyl, or aryl, which aryl may be aromatic or heteroaromatic. Aryl as used herein is for example phenyl, naphthyl or pyridyl.
$R^1$ and $R^2$ may also be combined with the carbon atom linking them to form a cycloaliphatic ring, preferably a 5- to 7-membered ring, such as cyclopentyl, cyclohexyl, methylcyclohexyl or cycloheptyl.
Alkyl R is preferably $C_1$-$C_4$alkyl, especially methyl. However, a particularly preferred meaning of R is hydrogen.
n is preferably an integer from 4 to 9, especially from 4 to 7.

Preferred dyes according to the present invention conform to the formula (4)

[structure of formula (4) showing a benzene ring with substituents Y, $R^4$, E, X, and B—NH—C(=Z)—$V^1$]

where
E is D—N=N— or

[structure showing (CN)$_2$C=C(CN)— group]

wherein D is the radical of a carbocyclic or heterocyclic diazo component,
X is hydrogen, $C_1$-$C_4$alkyl, $C_1$-$C_4$alkoxy, acylamino, halogen, $C_1$-$C_4$alkylsulfonylamino or a group of the formula —NH—CO—NHQ, in which Q is hydrogen, $C_1$-$C_4$alkyl or phenyl,
Y is hydrogen, halogen, $C_1$-$C_4$alkyl, $C_1$-$C_4$alkoxy, $C_1$-$C_4$alkoxy-$C_1$-$C_4$alkyl or $C_1$-$C_4$alkoxy-$C_2$-$C_4$alkoxy,
$R^4$ is $C_1$-$C_{12}$alkyl, $C_2$-$C_6$alkenyl or phenyl, or Y and $R^4$ together with the nitrogen atom and the two carbon atoms linking them form a 5- or 6-membered ring,
B is a radical of the formula

[chemical structures showing —(CH$_2$)$_m$—, —C(=O)—NH— phenyl, and various —C(=O)—N(H)— groups attached to substituted phenyl, cyclohexyl, and biphenyl radicals]

where m is an integer from 2 to 6,
Z is O or S and $V^1$ is —O—N=C(R$^5$)(R$^6$) or —N(—(CHR$^7$)$_{n'}$—)C(=O)— where $R^5$ and $R^6$ are each independently of the other $C_1$-$C_6$alkyl or $R^5$ and $R^6$ together with the carbon atom linking them form a cyclopentyl, cyclohexyl or cycloheptyl radical, $R^7$ is methyl or hydrogen and n' is 4, 5, 6 or 7.

Of these, it is the ones where E is D—N=N— which are particularly preferred.

If in the dyes of the formula (4) E is a radical D—N=N—, then D is the radical of a homocyclic or heterocyclic diazo component, for example from the group consisting of thienyl, phenylazothienyl, thiazolyl, isothiazolyl, 1,2,4-thiadiazolyl, 1,3,4-thiadiazolyl, benzothiazolyl, benzisothiazolyl, pyrazolyl, 1,2,3-triazolyl, 1,2,4-triazolyl and imidazolyl, or phenyl. Each of these systems may carry further substituents such as alkyl, alkoxy or alkylthio each of 1 to 4 carbon atoms, phenyl, electronegative groups such as halogen, in particular chlorine or bromine, trifluoromethyl, cyano, nitro, acyl, e.g. acetyl or benzoyl, carboalkoxy, in particular carbomethoxy or carbethoxy, alkyl sulfone of 1 to 4 carbon atoms, phenyl sulfone, phenoxysulfonyl, sulfonamido or arylazo, in particular phenylazo. Any 2 adjacent substituents on the ring systems mentioned may also together form further fused-on rings, for example phenyl rings or cyclic imides.

Preferably, D is a benzothiazolyl, benzisothiazolyl or phenyl radical which is unsubstituted or monosubstituted or disubstituted by one of the abovementioned radicals.

A benzothiazolyl or benzisothiazolyl D is in particular an unsubstituted or methyl-, methoxy-, chlorine-, bromine-, methylsulfonyl- or nitro-monosubstituted or polysubstituted radical.

The preferred meaning of D is phenyl which is substituted by up to 4 identical or different substituents selected from the abovementioned list. Of the substituents in the list, the electronegative ones are preferred. They can be in particular cyano, methylsulfonyl, ethylsulfonyl, nitro, chlorine, bromine, formyl, acetyl, benzoyl, carbomethoxy, carbethoxy, methoxy, ethoxy or phenylazo.

Alkyl for the purposes of this application is in general straight-chain, branched or cyclic alkyl, for example alkyl of 1 to 12 carbon atoms. The alkyl groups in question here are for example methyl, ethyl, propyl, isopropyl, butyl, isobutyl, tert-butyl, amyl, tert-amyl (1,1-dimethylpropyl), 1,1,3,3-tetramethylbutyl, hexyl, 1-methylpentyl, neopentyl, 1-, 2- or 3-methylhexyl, heptyl, n-octyl, tert-octyl, 2-ethylhexyl, n-nonyl, isononyl, decyl, dodecyl, cyclopentyl, cyclohexyl, methylcyclohexyl and the related isomers.

These alkyl radicals can be subsituted, for example by hydroxyl, alkoxy of 1 to 4 carbon atoms, in particular methoxy, halogen, such as bromine or chlorine, cyano or phenyl. Other suitable substituents are halogen, such as fluorine, chlorine or bromine, —CO—U and —O—CO—U, where U is alkyl of 1 to 6 carbon atoms or phenyl.

Suitable alkenyl radicals are those radicals derived from the abovementioned alkyl radicals by replacement of at least one single bond for a double bond. Suitable radicals are for example ethenyl and propenyl.

Suitable alkoxy is for example methoxy, ethoxy, propoxy, isopropoxy, n-butoxy, isobutoxy or tert-butoxy.

Examples of suitable substituted alkyl are: methoxymethyl, ethoxymethyl, ethoxyethyl, ethoxypropyl, n-propoxymethyl, isopropoxymethyl, butoxymethyl, butoxyethyl, butoxypropyl, ethoxypentyl, methoxybutyl, ethoxypentyl, 2-hydroxyethoxypentyl, cyanoethyl, hydroxyethyl and acetoxyethyl.

Equally, alkaline B can be straight-chain or branched or even substituted. Suitable alkylene B is for example ethylene, 1,3-propylene, 1,5-pentylene, 1,2-propylene, 1,2-butylene, 1,6-hexylene, 2-hydroxy-1,3-propylene or 2-chloro-1,3-propylene.

An acylamino X is for example a group of the formula

—NH—U—R⁸     (5)

where U is —CO— or —SO₂- and R⁸ is substituted or unsubstituted alkyl or phenyl.

The acyl radical is for example acetyl, propionyl, 2-chloroethylcarbonyl, 2-bromoethylcarbonyl, phenylcarbonyl, 2-methoxycarbonylethylcarbonyl, 2-ethoxycarbonylethylcarbonyl, methoxycarbonyl, ethoxycarbonyl, phenoxycarbonyl, methoxyethylcarbonyl, hydroxyethylcarbonyl, methylsulfonyl or ethylsulfonyl.

A group X of the formula —NH—CO—NHQ is for example ureido, methylureido, ethylureido or phenylureido.

Phenyl as used in this application is in general to be understood as meaning unsubstituted or substituted phenyl. Suitable substituents are for example C₁-C₄alkyl, C₁-C₄alkoxy, bromine, chlorine, nitro and C₁-C₄alkylcarbonylamino.

Halogen in this application is in general fluorine, bromine or in particular chlorine.

R⁴ and Y can form together with the nitrogen atom and the two carbon atoms linking them a 5- or 6-membered ring which may contain an oxygen atom as a further hetero atom. Suitable substituents for these rings are for example hydroxyl, methyl, methoxy, chlorine and phenyl. Preferably, R⁴ and Y together with the nitrogen atom and the two carbon atoms linking them form a 6-membered ring which is unsubstituted or carries 1 to 4 methyl groups. The compounds in question here are thus in particular di- or tetrahydroquinoline compounds having from 0 to 4 methyl groups.

In particularly preferred disperse dyes, D is a benzothiazolyl radical which is unsubstituted or monosubstituted or disubstituted by chlorine, or a phenyl radical which is monosubstituted or disubstituted by nitro, chlorine, cyano, methylsulfonyl, ethylsulfonyl or phenylazo.

The preferred meanings of X are hydrogen, methyl, methoxy, chlorine, bromine, acetylamino and ureido, of which hydrogen, methyl, chlorine and acetylamino are particularly preferred. Y is preferably chlorine, methyl, methoxy, methoxyethyl or methoxyethoxy or in particular hydrogen.

Particularly useful dyes according to the present invention conform to the formulae

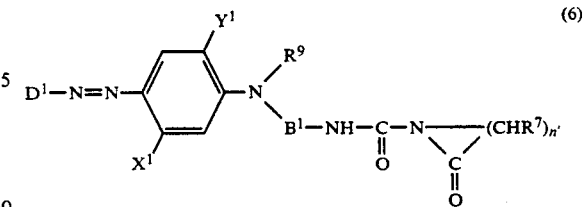 (6)

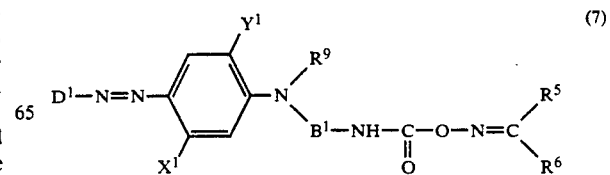 (7)

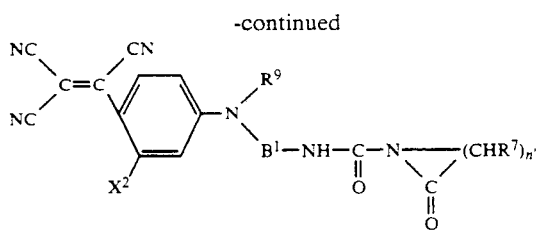

(8)

or

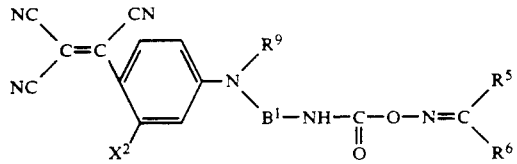

(9)

In the formulae (6) to (9) the symbols have the following meanings:

$D^1$ is a benzothiazolyl radical which is unsubstituted or disubstituted by chlorine, or is a phenyl radical which is monosubstituted or disubstituted by nitro, chlorine, cyano, methylsulfonyl, ethylsulfonyl or phenylazo, $X^1$ is hydrogen, methyl, methoxy, chlorine, bromine or acetylamino, $Y^1$ is chlorine, methyl, methoxy, methoxyethyl, methoxyethoxy or hydrogen, $Y^2$ is hydrogen, methyl, methoxy, chlorine or bromine, $R^9$ is $C_1$-$C_4$alkyl which is unsubstituted or substituted by hydroxyl, cyano, $C_1$-$C_4$alkoxy or phenyl.

$B^1$ is a radical of the formula

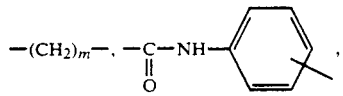

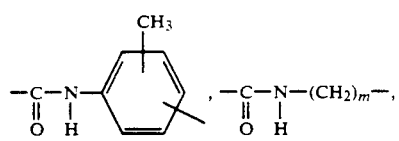

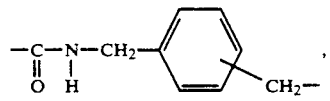

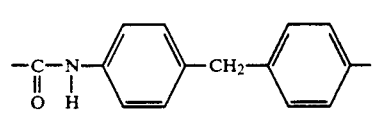

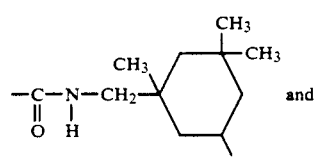

and

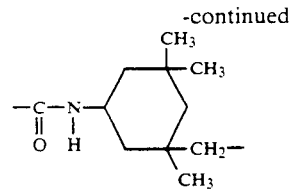

where m is an integer from 2 to 6, $R^5$ and $R^6$ are each independently of the other $C_1$-$C_6$alkyl or $R^5$ and $R^6$ together with the carbon atom linking them form a cyclopentyl, cyclohexyl or cycloheptyl radical, $R^7$ is methyl or hydrogen, and n' is 4, 5, 6 or 7.

The dyes of the formula (4) are prepared for example by reacting a diazotized amine of the formula $$D-NH_2 \quad (10)$$

or tetracyanoethylene with a compound of the formula

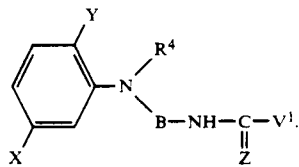

The compounds of the formula (10) are known or can be prepared in the same way as similar compounds.

The compounds of the formula (11) are new, and they form a further part of the subject-matter of the present invention. They are prepared for example by reacting a haloalkyl isocyanate or isothiocyanate of the formula $$Hal-B-N=C=Z \quad (12)$$

with an oxime or lactam of the formula $$V^1-H \quad (13)$$

and reacting the resulting reaction product of the formula

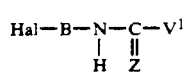

with a compound of the formula

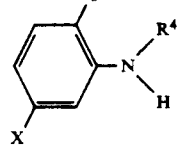

In the compounds (10) to (15), D, X, Y, $R^4$, B, Z, and $V^1$ are each as defined under the formula (4), and Hal is chlorine or bromine.

The compounds of the formulae (12) to (15) are known or can be prepared by known methods.

The reaction of compound (12) with compound (13) is carried out for example in an inert solvent and in the presence of a catalyst, for example diazabicyclooctane, and at about 0°-20° C. The components (12) and (13) can be used in a stoichiometric ratio, although an excess of one of the components is likewise possible. After the reaction has ended, compound (14) is isolated in a conventional manner, for example by crystallization. It is also possible to react compounds (12) and (13) with each other without a solvent.

The reaction of compound (14) with (15) is carried out for example in an inert organic solvent and in the presence of a base. Suitable inert organic solvents are for example compounds having a boiling point above 60° C., such as alcohols, ethers, esters, nitrobenzene, halobenzene, toluene, xylenes, etc. Of particular usefulness are alcohols, for example isopropanol, and the base used is for example sodium carbonate or potassium carbonate. The reaction of compound (14) with (15) can likewise also be carried out in the absence of a solvent.

The components (14) and (15) can be used in a stoichiometric ratio, but an excess of one of the components, preferably the compound (14), frequently proves to be more favourable.

The reaction temperature is about 50°-120° C., preferably between 60° and 100° C., and the reaction time is about 1-20 hours, depending on the temperature and the reactants. After the reaction has ended, any unconverted component (15) and the solvent are removed and the residue is purified if necessary, for example by recrystallization. The diazotization of compound (10) and the coupling with compound (11) are carried out in a conventional manner.

The reaction of compounds of the formula (11) with tetracyanoethylene is carried out in a conventional manner, preferably in an inert solvent at between about 20° and 100° C., the reaction components being used in approximately equivalent amounts.

A suitable inert solvent for the foregoing reaction is for example a halogen compound such as chloroform or chlorobenzene, an ether, an aromatic compound, such as benzene, toluene or xylene, in particular tetrahydrofuran or dimethylformamide.

The dyes of the formula (4) are isolated for example by pouring the reaction solutions into ice-water, filtering off the precipitated dye, and possibly washing and drying it.

A further method of preparing dyes of the formula (1) comprises reacting a dye of the formula F—H, where F is as defined under formula (1), with a compound of the formula (14). The reaction conditions correspond to the above-described conditions for reacting a compound of the formula (14) with a compound of the formula (15).

The above-described methods of preparation are suitable in particular for those compounds of the formula (4) in which $V^1$ is a lactam radical.

Dyes of the formula (1) or (4) where V or $V^1$ is an oxime radical are preferably prepared by reacting a compound of the formula $$\underset{X}{\overset{Y}{\underset{}{\bigodot}}}\overset{R^4}{\underset{B-NH_2}{N}} \quad (16)$$

or of the formula $$F-B-NH_2 \quad (18)$$

with a haloformic ester of an oxime of the formula $$\underset{Hal-C-O-N=C}{\overset{O}{\parallel}}\overset{R^1}{\underset{R^2}{}} \quad (17)$$

The symbols E, X, Y, $R^4$, B, F, Hal, $R^1$ and $R^2$ here are each as defined under the formulae (1) and (4).

The compounds of the formulae (16), (17) and (18) are known or can be prepared in the same way as similar compounds.

The reaction of compound (16) or (18) with compound (17) is preferably carried out in an inert organic solvent and in the presence of a base. Suitable inert organic solvents are for example hydrocarbons, halocarbons, alcohols, ethers, esters, nitrobenzene, halobenzene, toluene, xylenes, etc. Of particular suitability are halogenated hydrocarbons, e.g. dichloromethane, and the base used is for example sodium carbonate, potassium carbonate or an organic base, for example a trialkylamine.

The components (16) or (18) and (17) can be used in a stoichiometric ratio, but an excess of one of the components, preferably of component (17), has frequently proved to be more favourable.

The reaction temperature is about 0° to 60° C., preferably between 10° and 30° C., and the reaction time is about 0.1-2 hours, depending on the temperature and the reactants. After the reaction has ended, any unconverted component (17) and the solvent are removed, and the residue is purified if necessary.

Dyes of the formula (1) or (4) in which B is a bridge member of the formula $$-\underset{O}{\overset{}{\underset{\parallel}{C}}}-\underset{H}{\overset{}{\underset{|}{N}}}-W-$$

where W is a divalent organic radical, are preferably prepared by reacting a diisocyanate of the formula $$OCN-W-NCO \quad (19)$$

in any desired order with a dye which contains a reactive —OH or —NH group and with an oxime of the formula (2) or a lactam of the formula (3). The reaction conditions correspond to the known conditions for the reaction of isocyanates with OH— or $$\underset{/}{\overset{\diagdown}{}}NH\text{-containing compounds.}$$

The dyes according to the present invention can be used for dyeing and printing cellulosic and in particular synthetic hydrophobic fibre materials, in particular textile materials. Textile materials composed of blend fabric which contains such cellulosic or synthetic hydrophobic textile materials can likewise be dyed or printed with the aid of the compounds according to the present invention.

Cellulosic textile materials are in particular those composed of cellulose acetate and cellulose triacetate.

Synthetic hydrophobic textile materials consist in particular of linear aromatic polyesters, for example polyesters formed from terephthalic acid and glycols, in particular ethylene glycol, or condensation products of terephthalic acid and 1,4-bis(hydroxymethyl)-cyclohexane; of polycarbonates, for example, those formed from α,α-dimethyl-4,4'-dihydroxydiphenylmethane and phosgene; and of fibres based on polyvinyl chloride or polyamide.

The compounds according to the present invention are applied to the textile materials by known dyeing methods. For example, polyester fibre materials are dyed by the exhaust method from aqueous dispersion in the presence of customary anionic or nonionic dispersants and in the presence or absence of customary swelling agents (carriers) at temperatures between 80° and 140° C. Fibre materials made of cellulose acetate are preferably dyed between about 65° and 85° C. and those made of cellulose triacetate at temperatures of up to 115° C.

Some of the dyes according to the present invention however, are suitable in particular for dyeing by the thermosol process.

For application of the dyes according to the present invention, the textile material mentioned can be in a wide range of states of processing, for example in the form of a fibre, yarn, web, woven fabric or knitted fabric.

It is advantageous to convert the dyes according to the present invention into a dye preparation before use. To this end, the dye is ground so that its particle size is on average between 0.1 and 10 microns. The grinding can be carried out in the presence of dispersants. For example, the dried dye is ground with a dispersant or kneaded in paste form with a dispersant and then dried under reduced pressure or by spray drying. The preparations thus obtained can be used for dyeing and printing on addition of water.

In printing, use is made of customary thickeners, for example modified or unmodified natural products, for example alginates, British gum, gum arabic, crystal gum, carob bean flour, tragacanth, carboxymethylcellulose, hydroxyethylcellulose or starch, or synthetic products, for example polyacrylamides, polyacrylic acid or copolymers thereof or polyvinyl alcohols.

After the actual dyeing process, the dyeings obtained are subjected to a thermal aftertreatment, for example by heating them to a temperature between 100° and 240° C., preferably between 180° and 220° C., for 30 to 500 seconds, preferably 45 to 200 seconds. This thermal aftertreatment significantly improves the fastness of the dyeings to thermomigration, since the dyes are converted by elimination of appropriate radicals into dyes having isocyanate or isothiocyanate groups. These groups can then react with suitable groups on the fibre or of chemicals present on the fibre, for example with amine or hydroxyl groups.

If the dyeings have been prepared by the thermosol process, which normally includes a thermofix stage at about 180°-210° C., no separate thermal aftertreatment is necessary for some of the dyes according to the present invention. Otherwise, it is advisable to carry out the heat fixation at elevated temperature, for example at 200° to 230° C. and/or for a prolonged period, for example 120 to 300 seconds.

With some of the dyes according to the present invention, temperatures of 110° to 140° C. are sufficient to fix them. With these dyes, therefore, the thermal aftertreatment can be integrated into an HT dyeing process or be dispensed with entirely.

The dyes according to the present invention confer on the materials mentioned, in particular polyester material, level yellow to blue shades having very good end-use fastness properties, especially good light fastness, sublimation fastness, fastness to dry heat setting and pleating, chlorine fastness and wet fastness properties, such as water, perspiration and wash fastness; the dyeings are further remarkable for good rub fastness and fastness to dry heat setting and pleating. What is more, very strong dyeings are obtained.

The Examples which follow illustrate the invention without limiting it. Parts and percentages are by weight, unless otherwise stated. The temperatures are given in degrees Celsius.

EXAMPLE 1

A conventionally prepared diazonium chloride solution of 17.3 g (0.1 mol) of 2-chloro-4-nitroaniline is added dropwise at 7°-10° C. to a solution of 19.7 g (0.1 mol) of N-2-aminoethyl-N-ethylaniline (prepared by hydrolysis of phthalimidoethyl-ethylaniline in aqueous hydrogen bromide) in 1000 ml of acetic acid in the course of 15 minutes. After 2 hours' stirring, the violet-red suspension is filtered with suction, the filter cake is slurried in 400 ml of water, the slurry is brought to about pH 11 with 60 ml of 30 per cent sodium hydroxide solution and filtered with suction, and the filter cake is washed and dried in a vacuum cabinet. 27.6 g (79.3% of the calculated amount) are obtained of the red dye of the formula

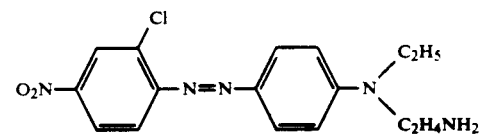

as a grey powder of melting point 133°-134° C.

17.4 g (0.05 mol) of this aminoethyl dye are dissolved in 200 ml of dichloromethane. 5.5 g of triethylamine (0.055 mol) are added, followed dropwise in the course of 20 minutes at a temperature maintained at a maximum not higher than 25° C. by 25 ml of the crude chloroformic ester of acetoneoxime (about 10% excess). After half an hour, the reaction solution is extracted first with water, then with dilute hydrochloric acid and finally again with water. Evaporation of the dichloromethane layer, washing the residue with isopropanol and drying leaves 20.9 g (93.6% of theory) of the dye of the formula

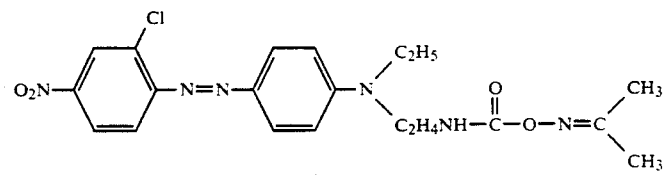

as a violet powder of melting point 148°–149°.

EXAMPLE 2

Example 1 is repeated with the chloroformic ester of acetoneoxime replaced by an equivalent amount of that of 2-butanoneoxime, affording the dye of the formula

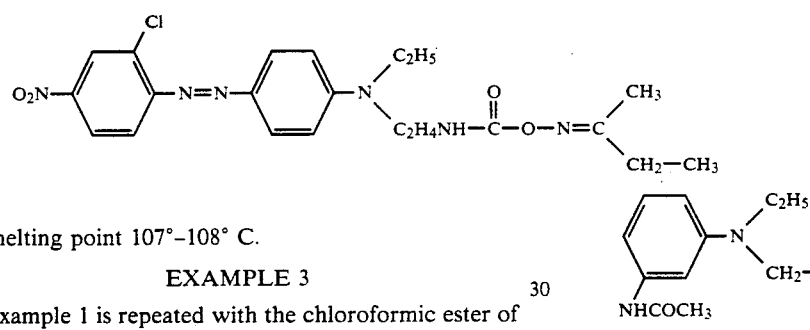

of melting point 107°–108° C.

EXAMPLE 3

Example 1 is repeated with the chloroformic ester of acetoneoxime replaced by an equivalent amount of that of cyclohexanoneoxime, affording the dye of the formula

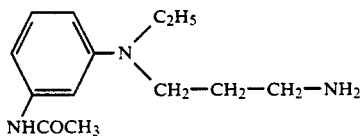

of melting point 152°–154° C.

EXAMPLE 4

Example 1 is repeated with aminoethyl-ethylaniline replaced by an equivalent amount of N-aminoethyl-N-ethyl-m-toluidine (obtained by hydrolysis of the succinimidoethyl compound), affording the dye of the formula

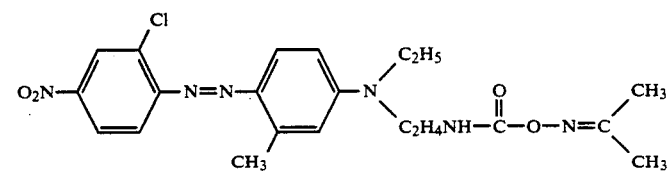

of melting point 68° C.

EXAMPLE 5

21.5 g (0.093 mol) of 3-N-cyanoethyl-N-ethylaminoacetanilide are hydrogenated at 70°–75° C. in 100 ml of anhydrous ethanol and 30 g of liquid ammonia under an initial pressure of 150 bar of hydrogen in the presence of 4.3 g of Raney nickel. The absorption of hydrogen ceases after 1.5 hours. The catalyst is filtered off, and the solution is evaporated, leaving 22.5 g (approximately the calculated amount) of the crude compound of the formula

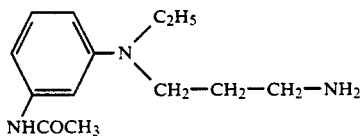

as a highly viscous brown oil.

5.7 g (about 0.024 mol) of this crude coupling component are then reacted in 200 ml of 2N sulfuric acid with the diazonium chloride solution obtained from 3.45 g (0.02 mol) of 2-chloro-4-nitroaniline at 0°–10° C. for 2 hours. The brown dye is then filtered off, washed with 2N sulfuric acid and suspended in 200 ml of water, and the suspension is brought to pH 10 with sodium hydroxide. The suspension if filtered with suction, and the filter cake is washed with water and dried, leaving 5.8 g (69% of theory) as a greenish brown, chromatographically nonuniform powder of melting point 144°–147° (sintering at 105° C.).

2.1 g (0.05 mol) thereof are dissolved in 20 ml of dichloromethane and admixed with 0.76 ml (about 10% excess) of triethylamine and then in the course of 10 minutes at 22°–25° C. with 5 ml of the crude chloroformic ester of acetoneoxime. After stirring for one hour, the starting material is no longer detectable in a thin layer chromatogram. The dichloromethane solution is evaporated together with 9 g of silica gel, and the mixture is purified over a silica gel column using ethyl acetate as eluent, giving 0.9 g of the dye of the formula

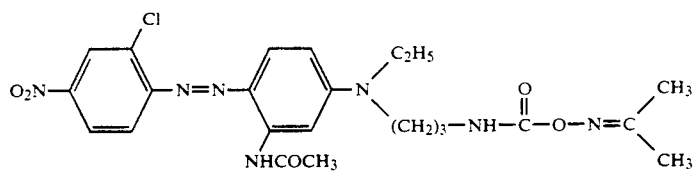

as a brown powder of melting point 167°–168°, the nuclear magnetic resonance spectrum of which confirms the structure.

EXAMPLES 6–9

The same method is used to prepare from the coupling components described in Example 5, the diazo components identified in column 1 of the table below and the chloroformic esters of the ketoximes listed in column 2 the following dyes:

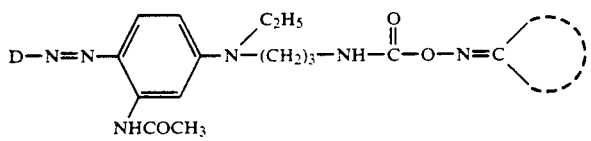

| Example | D | Ketoxime | Colour | Melting point |
|---|---|---|---|---|
| 6 | 2-Chloro-4-nitrophenyl | Cyclohexanoneoxime | Red | 135–136° C. |
| 7 | 2-Bromo-4,6-dinitrophenyl | Acetoneoxime | Violet blue | 108–113° C. |
| 8 | Mixture of 5,6- and 6,7-dichloro-2-benzothiazolyl | Acetoneoxime | Ruby | 76–79° C. |
| 9 | 2,5-Dicarbomethoxy-4-methyl-2-thienyl | Acetoneoxime | Reddish violet | 66–68° C. |

EXAMPLE 10

A mixture of equal parts of the dyes described in Examples 1, 2 and 3 is converted in a conventional manner by sand milling with twice the amount of commercial dispersant of the dinaphthylmethanedisulfonate type into a 5 per cent aqueous dispersion. This formulation is used to prepare in a conventional manner a 1 per cent (with respect to dye) carrier dyeing (95° C., carrier based on trichlorobenzene and biphenyl) on polyethylene terephthalate fabric, which is then reduction-cleared. The deep red fabric is very highly rub- and wash-fast.

If, however, to test the fastness to thermomigration the fabric is heated to 160° C. for 45 seconds, the rub fastness deteriorates very badly and the usual wash test at 60° C. produces very deep staining of in particular the cellulose acetate and polyamide adjacent fabrics. The picture is still worse if the fabric is finished with a textile softener of the distearyldiethylenetriamine type prior to the thermomigration test.

If, however, the dyed fabric is heated to 210° C. for 60 seconds prior to reduction clearing, then the thermomigration test had virtually no effect, with or without softener, on the rub and wash fastness properties and only very little dye is extractable from the fabric even on extracting with dimethylformamide at 95° C. for one hour.

EXAMPLE 11

The 5 per cent dye formulation described in Example 10 is used in an HT process at 130° C. in a conventional manner to prepare a 1 per cent of dye on weight of fibre dyeing, which is then reduction cleared.

The thermomigration fastness tested in the manner described in Example 10 is found to be very good. The same result is obtained with an HT dyeing with a 5 per cent dispersion of the dye described in Example 1.

EXAMPLE 12

A deep red dyeing prepared with a 5 per cent dispersion of the dye of Example 1 by padding and thermofixing at 200° C. is found to be very fast to thermomigration in the tests described.

EXAMPLE 13

12.0 g of anhydrous ε-caprolactam are dissolved in 30 ml of toluene, and the solution is slowly added dropwise at room temperature to a mixture of 17.8 g of toluylene 2,4-diisocyanate and 0.05 g of diazabicyclooctane. After 22 hours' stirring at room temperature and 6 hours' stirring at 80° C., the solution is left to stand at room temperature for several days. The resulting precipitate is filtered off and dried, leaving 6.1 g of colourless crystals of the formula

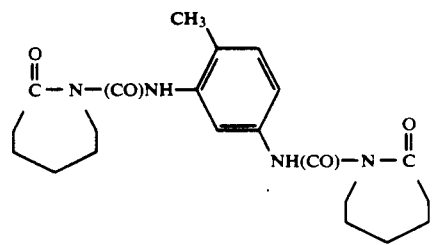

and of melting 164°–166° C.

The mother liquor contains about 29 g of product of the formula

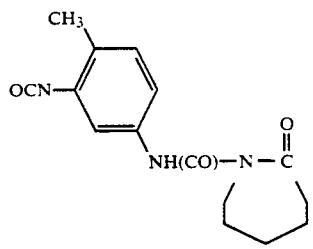

as toluene solution.

A quarter of this solution is taken and the solvent is distilled off.

50 ml of anhydrous dimethylformamide are added to the residue, followed by 6.3 g of the dye of the formula

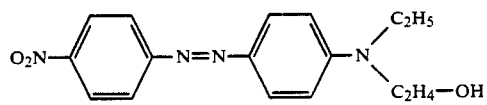

The mixture is stirred at room temperature for 48 hours and then discharged onto 500 g of ice-water. Filtering, washing and drying gives 11.0 g of crude product. To purify it, it is suspended in 80 ml of methanol and stirred under reflux for 3 hours. Filtering (hot), washing and drying gives brownish red crystals of the formula

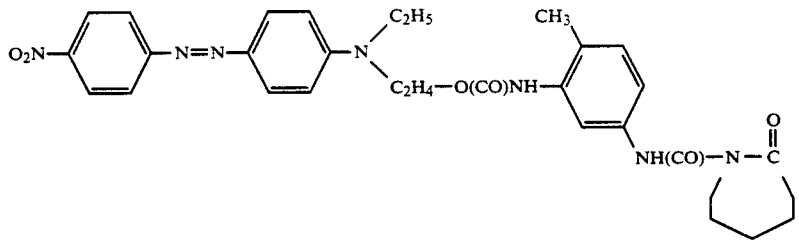

and of melting point 169°-173° C. The dye dyes polyester material in scarlet shades.

EXAMPLE 14

A toluene solution containing 29 g of the monoisocyanate described in Example 13 is added dropwise at room temperature to 14.1 g of N-ethyl-N-hydroxyethylaniline. After 6 hours' stirring at 80° C., the solvent is distilled off. The colourless mass left behind conforms to the formula

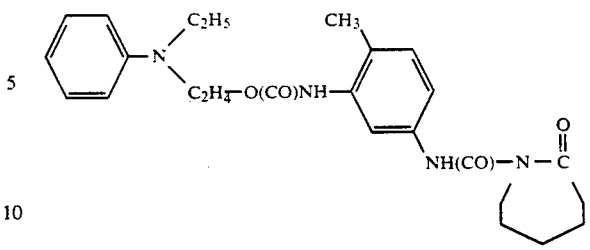

and can be used as a coupling component without further purification.

EXAMPLE 15

3.3 g of 2-cyano-4-nitroaniline are conventionally diazotized in sulfuric acid and coupled at 0°-10° C. onto a mixture containing 0.02 mol of the coupling component of Example 14, 50 ml of acetic acid and 50 g of ice. After the coupling has ended, 300 ml of water are added. After stirring at room temperature for 1 hour, the mixture is filtered and the filter residue is washed. To purify the crude product, it is suspended in 100 ml of methanol and stirred under reflux for 2 hours. It is then filtered off hot and washed with methanol. Drying at 40° C. leaves 10.2 g of a blackish green powder of the formula

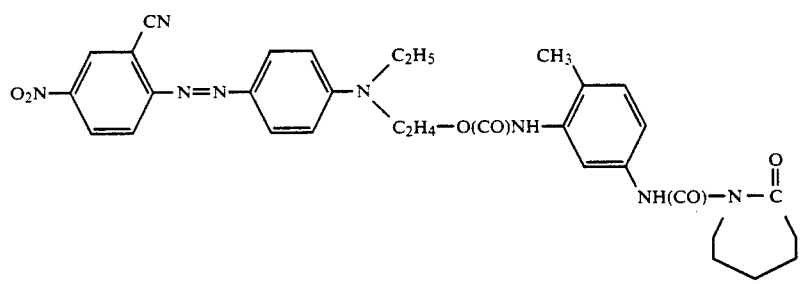

of melting point 125°-130° C. The dye dyes polyester material in ruby shades.

EXAMPLE 16

8.3 g of N-ethyl-N-hydroxyethylaniline are slowly added dropwise at 10° C. to 8.9 g of toluylene 2,4-diisocyanate, 0.05 g of diazabicyclooctane and 10 ml of dimethylformamide. 5.7 g of ε-caprolactam are added after 6 hours' stirring at room temperature. The mixture is then stirred at 80° C. for a further 6 hours.

The reaction mixture which contains the intermediate of the formula two main zones. The leading zone, which has an $R_f$ value of 0.9, contains the substance of the formula

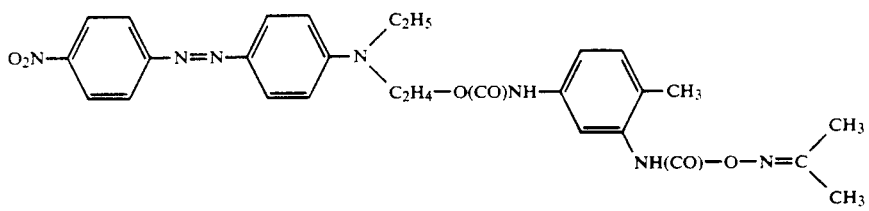

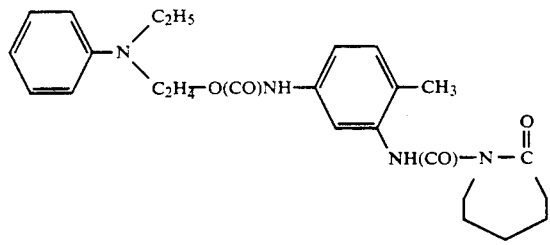

can be used in this form as coupling component.

EXAMPLE 17

4.6 g of 2,4-dinitroaniline are conventionally diazotized in sulfuric acid and coupled at 0°–10° C. onto a mixture containing about 7.2 g of the coupling component described in Example 16 in 100 ml of 80% acetic acid. After the reaction mixture has been diluted with 400 g of ice-water, it is filtered, and the filter residue is washed and dried. 12.7 g are obtained of black crystals of the formula

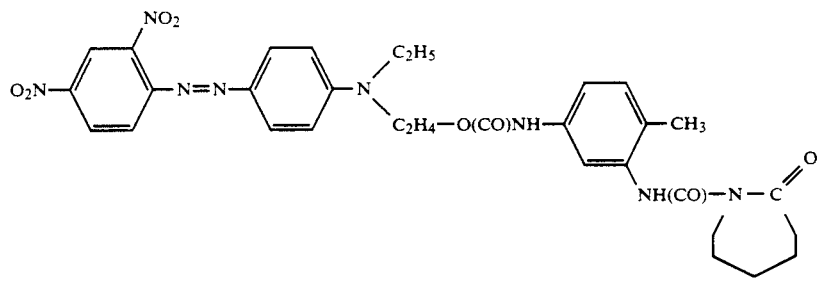

of melting point 185°–190° C.

The dye dyes polyester material in ruby shades.

EXAMPLE 18

6.3 g of the dye of the formula

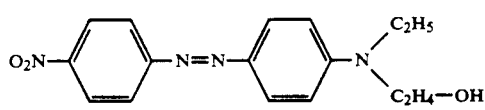

and 0.05 g of diazabicyclooctane are dissolved in 50 ml of anhydrous dimethylformamide. 7.0 g of toluylene 2,4-diisocyanate are slowly added dropwise at 10° C. After 8 hours' stirring at room temperature, 5.1 g of acetoneoxime are added. After stirring overnight, the reaction mixture is discharged onto 500 g of ice-water. Filtering, washing and drying gives 10.8 g of an orange powder (product mixture) whose thin layer chromatogram on silica gel with 4:1 chloroform/acetone shows The crude product has an absorption maximum at 478 nm (in ethanol) and dyes polyester material in scarlet shades.

EXAMPLE 19

A 1 per cent solution of the dye described in Example 18 is prepared in N-methylpyrrolidone. This solution is used in an HT process to prepare a 0.5% of dye on weight of fibre dyeing on polyester.

The thermomigration fastness (test as described in Example 10) is found to be very good if the dyed fabric is heated to 230° C. for 1 minute prior to reduction clearing.

EXAMPLE 20

19.2 g of p-nitroaniline are conventionally diazotized in hydrochloric acid and coupled at 0°–10° C. onto a mixture containing 34.6 g of 3-(N-cyanoethyl-N-hydroxyethyl)aminoacetanilide in 300 ml of glacial acetic acid and 400 g of ice-water. The mixture is adjusted to pH 3 with 30% sodium hydroxide solution at 0°–10° C. Filtering, washing and drying gives 50.1 g of a crude product. To purify the crude product, it is suspended in 300 ml of tertiary-butyl methyl ether, and the suspension is stirred under reflux for 2 hours. Filtering (hot), washing and drying gives 47.8 g of dark red crystals of the formula

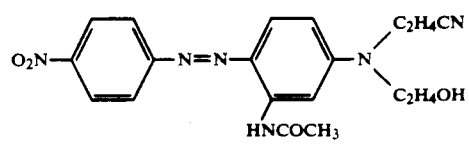

of melting point 164°–165° C.

1.6 g of this dye and 0.05 g of diazabicyclooctane are dissolved in 20 ml of anhydrous dimethylformamide. 0.9 g of toluylene 2,4-diisocyanate are slowly added dropwise at room temperature. After 48 hours' stirring at room temperature, 1.4 g of anhydrous caprolactam are added.

After 12 hours' stirring at 80° C., the mixture is discharged onto 300 g of ice-water. Filtering, washing and drying gives 2.5 g of a brownish red powder (product mixture) of melting point 110°–150° C. Thin layer chromatogram on silica gel with ethyl acetate shows two main zones having an $R_f$ value of 0.75 and 0.6 respectively.

The product mixture dyes polyester material in scarlet shades.

1.2 g of the above-described reaction mixture are chromatographed with ethyl acetate over a column of 230 g of silica gel. The fraction which has an $R_f$ of 0.75 yields 0.2 g of a brownish red powder of the formula

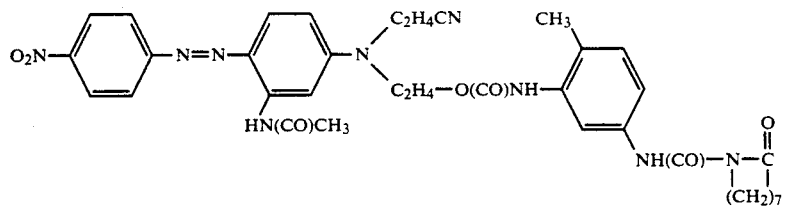

and of melting point 85°–105° C.

The dye dyes polyester material in scarlet shades.

EXAMPLE 21

The product mixture described in Example 20 is formulated as a 5% aqueous dispersion (cf. Example 10). This dispersion is used to prepare a thermosol dyeing on polyester (10 g of dye/l, liquor pickup 50%, fixing temperature 230° C.).

The dyeing obtained is very fast to thermomigration (test as described in Example 10).

Similar results are obtained on replacing the product mixture of Example 20 by the purified dye fraction of this example.

EXAMPLES 22–77

The method described in Examples 13, 15 and 20 is used to prepare, as individual compounds and in mixtures, the dyes listed in the following table:

| Example | Dye | Shade on polyester |
|---|---|---|
| 22 | (structure) | red |
| 23 | (structure) | red |
| 24 | (structure) | scarlet |

| Example | Dye | Shade on polyester |
|---|---|---|
| 25 | O₂N–C₆H₄–N=N–C₆H₄–N(C₂H₅)–CH₂CH₂–O–C(O)–NH–CH₂–[3,3,5-trimethylcyclohexyl]–NH–C(O)–N(azepan-2-one) | scarlet |
| 26 | [2-CN-4-NO₂-C₆H₃]–N=N–C₆H₄–N(C₂H₅)–CH₂CH₂–O–C(O)–NH–[3,5,5-trimethylcyclohexyl]–CH₂–NH–C(O)–O–N=C(CH₃)(C₂H₅) | ruby |
| 27 | O₂N–C₆H₄–N=N–C₆H₄–N(C₂H₅)–CH₂CH₂–O–C(O)–NH–(CH₂)₆–NH–C(O)–O–N=C(CH₃)–CH₂–CH(CH₃)₂ | scarlet |
| 28 | O₂N–C₆H₄–N=N–C₆H₄–N(C₂H₅)–CH₂CH₂–O–C(O)–NH–(CH₂)₆–NH–C(O)–N(azepan-2-one) | scarlet |
| 29 | [2,4-(NO₂)₂-6-Br-C₆H₂]–N=N–[3-NHCOCH₃-C₆H₃]–N(C₂H₅)–CH₂CH₂–O–C(O)–NH–C₆H₄–NH–C(O)–O–N=cyclohexylidene | violet |
| 30 | [5-NO₂-benzisothiazol-3-yl]–N=N–C₆H₄–N(C₂H₅)–CH₂CH₂–O–C(O)–NH–[2-Me-5-(NHCO–N=C=O-cycloheptyl)-C₆H₃] | blue |

-continued

| Example | Dye | Shade on polyester |
|---|---|---|
| 31 | [structure] | blue |
| 32 | [structure] | reddish blue |
| 33 | [structure] | reddish blue |
| 34 | [structure] | reddish blue |
| 35 | [structure] | ruby |

-continued

| Example | Dye | Shade on polyester |
|---|---|---|
| 36 | (structure: 2-cyano-4-nitrophenyl azo — N(C2H5)(C2H4—O(CO)—NH—CH2—C6H4—CH2—NH(CO)—N-caprolactam) phenyl) | ruby |
| 37 | (structure: 5,6-dichlorobenzothiazol-2-yl azo — phenyl—N(C2H5)(C2H4—O(CO)NH—(4-methylphenyl-NH(CO)—N-caprolactam))) | red |
| 38 | (structure: 5,6-dichlorobenzothiazol-2-yl azo — 2-methylphenyl—N(C2H5)(C2H4—O(CO)NH—(4-methylphenyl-NH(CO)—N=C(C2H5)CH3))) | ruby |
| 39 | (structure: H5C2—S—C(=S)—N=N— thiadiazole linked azo — phenyl(HN(CO)CH3)—N(C2H5)(C2H4—O(CO)NH—(4-methylphenyl-NH(CO)—N-caprolactam))) | red |
| 40 | (structure: H5C2—S—C(=S)—N=N— thiadiazole linked azo — phenyl(HN(CO)CH3)—N(C2H5)(C2H4—O(CO)NH—CH2—C6H4—CH2—NH(CO)—N-caprolactam)) | red |
| 41 | (structure: thiophene with CH3, COOCH3, CH3OOC substituents — azo — phenyl(HN—CO—CH3)—N(C2H5)(C2H4—O(CO)NH—(CH2)6—NH(CO)—N-caprolactam)) | red |

| Example | Dye | Shade on polyester |
|---|---|---|
| 42 | 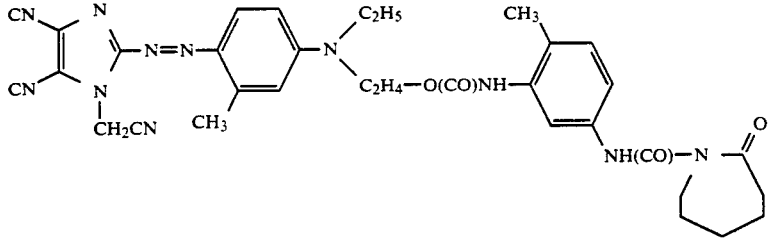 | red |
| 43 | 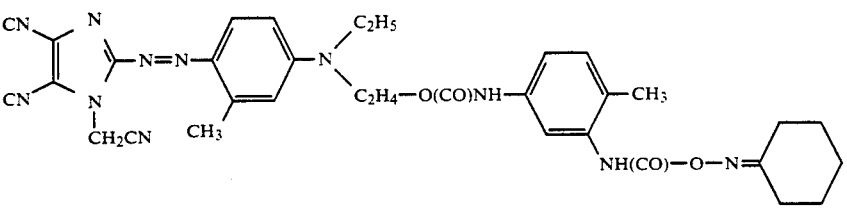 | red |
| 44 | 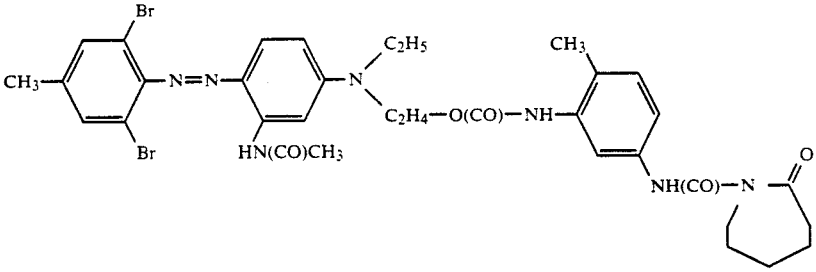 | yellow |
| 45 | 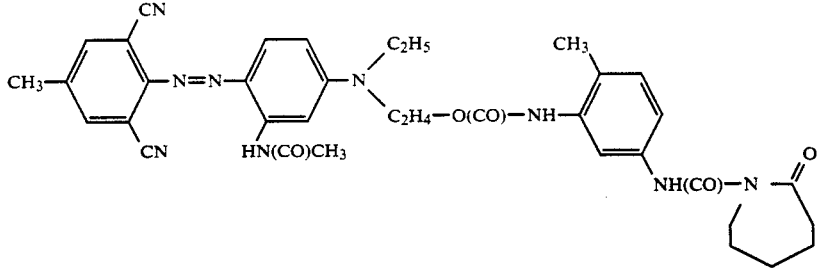 | red |
| 46 | 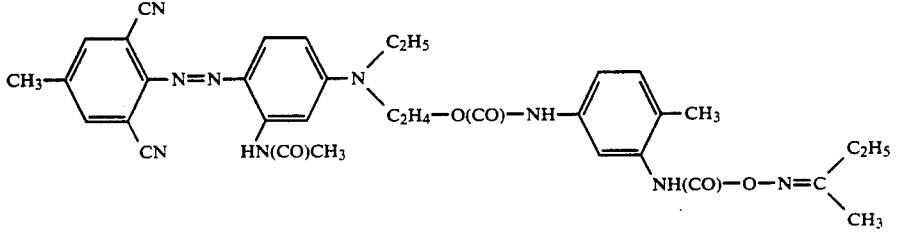 | red |

| Example | Dye | Shade on polyester |
|---|---|---|
| 47 | 2-[(2,6-dicyano-4-nitrophenyl)azo]-N-ethyl-N-[2-[[[(3-methyl-5-(2-oxo-1-azepanylcarbonylamino)phenyl)amino]carbonyl]oxy]ethyl]-3-methylaniline derivative | reddish blue |
| 48 | analogous structure with propan-2-one O-carbamoyl oxime terminus | reddish blue |
| 49 | 2,4-dinitro-6-nitroso phenylazo derivative with -C2H4-O(CO)NH-(CH2)6-NH(CO)-O-N=C(CH3)2 chain and HN(CO)CH3 | blue |
| 50 | 2,4-dinitro-6-cyano phenylazo derivative with caprolactam end group and HN(CO)CH3 | blue |
| 51 | 2,4-dinitro-6-cyano phenylazo derivative with propan-2-one oxime carbamate end group and HN(CO)CH3 | blue |
| 52 | 2,4-dinitro-6-bromo phenylazo derivative with -C2H4-O(CO)NH-(CH2)6-NH(CO)-O-N=C(CH3)2 chain and HN(CO)CH3 | reddish blue |

-continued

| Example | Dye | Shade on polyester |
|---|---|---|
| 53 | O₂N–C₆H₃(CN)–N=N–C₆H₄–N(C₂H₅)–C₂H₄–O(CO)NH–(CH₂)₆–NH(CO)–N(caprolactam) | red |
| 54 | (3-CH₃-4-CN-isothiazol-5-yl)–N=N–C₆H₃(HN(CO)CH₃)–N(C₂H₅)–C₂H₄–O(CO)NH–C₆H₃(CH₃)–NH(CO)–N(caprolactam) | bluish red |
| 55 | (5-O₂N-3-COOC₂H₅-thiophen-2-yl)–N=N–C₆H₃(CH₃)–N(C₂H₅)–C₂H₄–O(CO)NH–C₆H₃(CH₃)–NH(CO)–N(caprolactam) | blue |
| 56 | (2,4-dinitrophenyl)–N=N–C₆H₄–N(C₂H₅)–C₂H₄–O(CO)–NH–C₆H₃(CH₃)–NH(CO)–O–N=cyclohexylidene | ruby |
| 57 | (4-O₂N-C₆H₄)–N=N–C₆H₄–N(C₂H₅)–C₂H₄–O–CO–NH–C₆H₃(CH₃)–NH(CO)–N(caprolactam) | scarlet |
| 58 | (4-O₂N-C₆H₄)–N=N–C₆H₃(HN(CO)CH₃)–N(C₂H₄CN)–C₂H₄–O–CO–NH–C₆H₃(CH₃)–NH(CO)–N(caprolactam) | scarlet |

-continued
| Example | Dye | Shade on polyester |
|---|---|---|
| 59 | 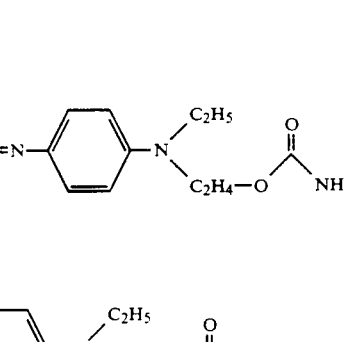 | scarlet |
| 60 | | scarlet |
| 61 | | scarlet |
| 62 | 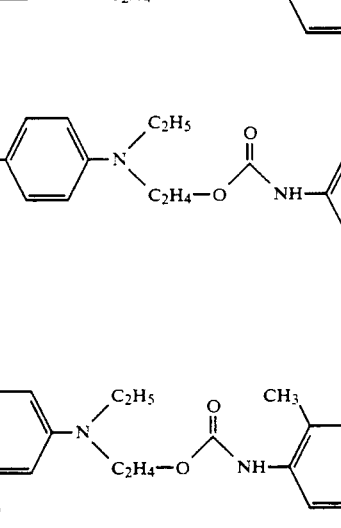 | red |
| 63 | | ruby |
| 64 | 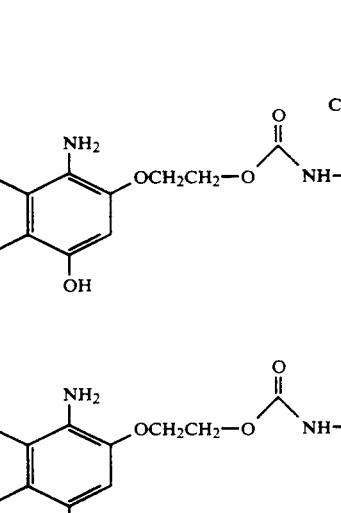 | red |
| 65 | 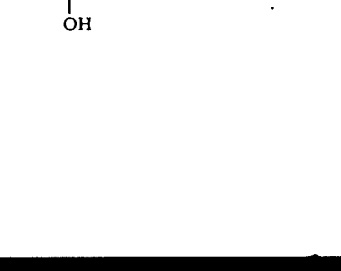 | red |

| Example | Dye | Shade on polyester |
|---|---|---|
| 66 | 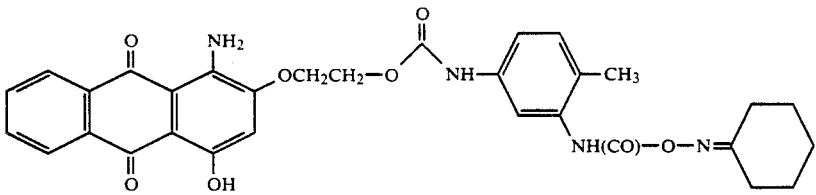 | red |
| 67 | 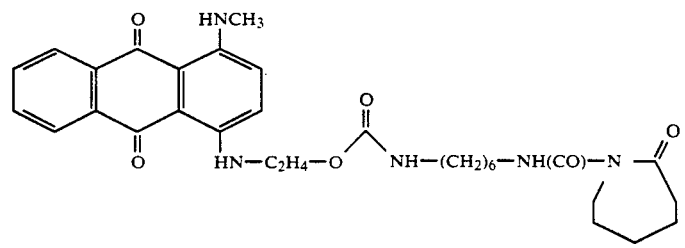 | blue |
| 68 | 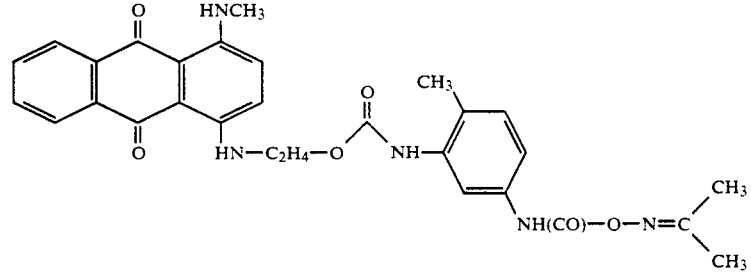 | blue |
| 69 | 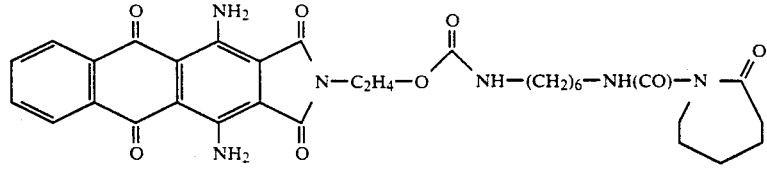 | blue |
| 70 | 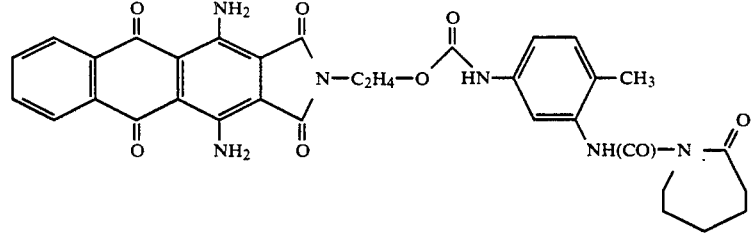 | blue |
| 71 | 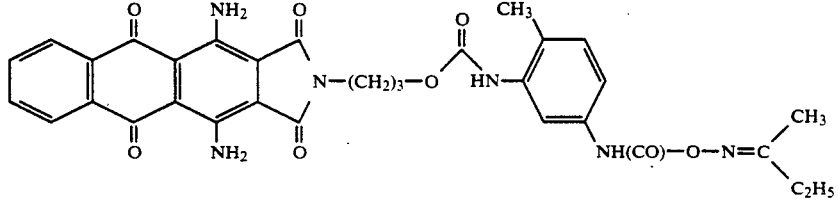 | blue |

-continued
| Example | Dye | Shade on polyester |
|---|---|---|
| 72 | 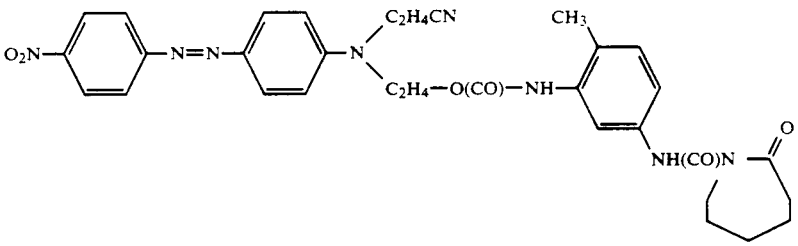 | orange |
| 73 | 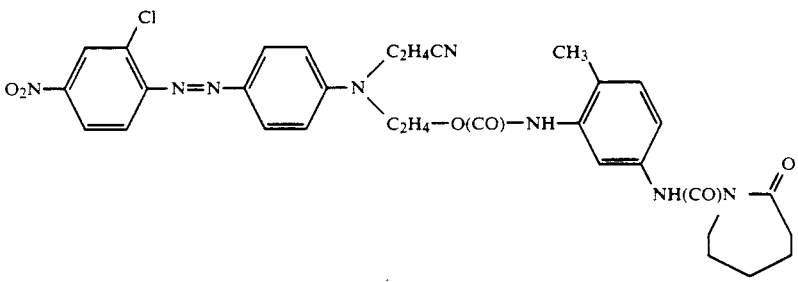 | scarlet |
| 74 | 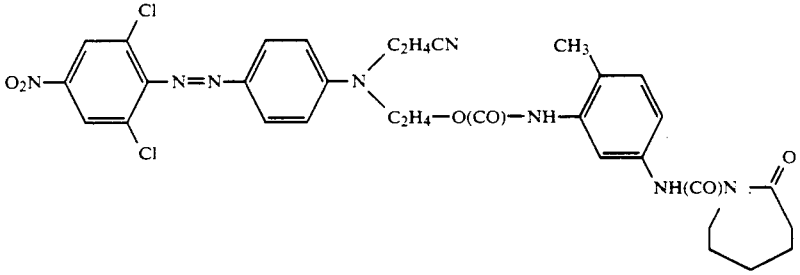 | brown |
| 75 | 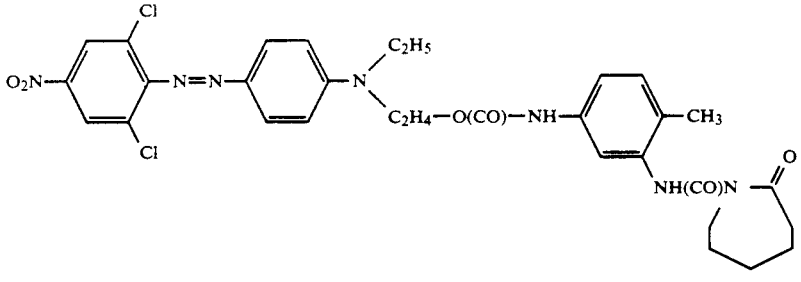 | brown |
| 76 | 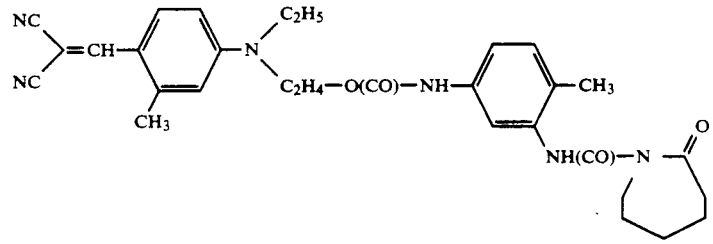 | yellow |

| Example | Dye | Shade on polyester |
|---|---|---|
| 77 | | yellow |
| 78 | | yellow |
| 79 | | yellow |

EXAMPLES 80–82

70.5 g of N-cyanoethyl-N-ethylaniline of a purity of 98.7% are hydrogenated with Raney nickel in anhydrous ethanol in the presence of ammonia by the method described in Example 5. The absorption of hydrogen ceases after 2.5 hours. The catalyst is filtered off and the solution is concentrated to leave a crude oily amine of the formula (64 g≈90% of theory)

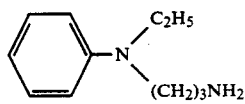

which is used without purification for coupling by the method of Example 5 with an equivalent amount of the diazonium salt solution prepared from 2-chloro-4-nitroaniline to obtain the crude amino dye of the formula

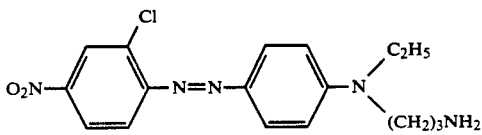

as a brown powder of melting point 205°–208° C.

The reaction of this aminopropyl dye with the chloroformic esters of the ketoximes listed in column 2 of the table below gives the following red dyes:

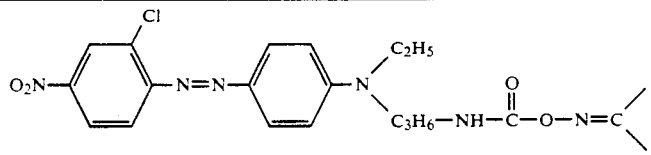

| Example | Ketoxime | Melting point |
|---|---|---|
| 80 | Acetoneoxime | 223-5° (sint. 219) |
| 81 | Cyclohexanoneoxime | amorphous |
| 82 | Methyl isobutyl ketone oxime | amorphous |

EXAMPLE 83

21.3 g of 2-bromo-3-cyano-4,6-diaminopyridine and 60 g of 1,2-diaminoethane are stirred in an autoclave at 125° and 2 bar for 2 hours, and excess diaminoethane is evaporated off under reduced pressure. The crude residue of 32.8 g contains, diaminoethane hydrobromide aside, the compound of the formula

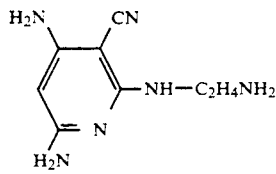

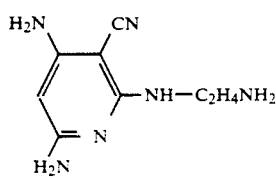

partly as hydrobromide, 4 g of the residue are coupled at 0°-5° in the course of 2 hours to the diazonium salt solution, in 80 ml of 80 per cent acetic acid, prepared from 1.83 g of 2,4-dinitroaniline, the dye is filtered off with suction and suspended in water, the suspension is brought to pH 11-12 with sodium hydroxide and filtered with suction, and the filter residue is washed with water and dried. 3.0 g are obtained of the red aminoethyl dye of the formula

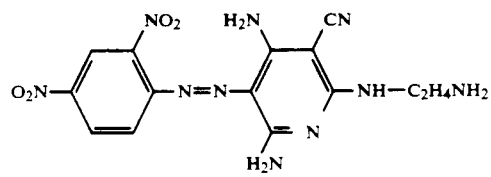

which does not melt below 230° C.

1.5 g (~0.004 mol) thereof are suspended in 20 ml of dichloromethane. 0.6 ml (0.0044 mol) of triethylamine are added, followed dropwise for about 20 minutes by 0.0088 mol of the chloroformic ester of acetoneoxime, and the mixture is stirred at room temperature for 1.5 hours. Unconverted aminoethyl dye is filtered off, the chloroformic ester is destroyed with a little ammonia, and the mixture is concentrated under reduced pressure.

Chromatography over silica gel with ethyl acetate as eluent gives the red dye of the formula

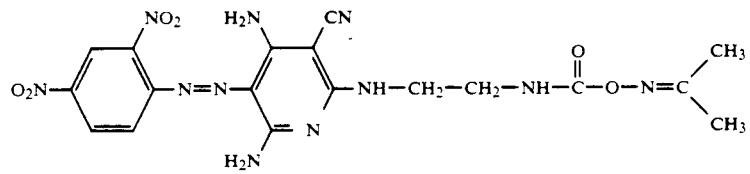

as a brown powder of melting point 205°-206°.

EXAMPLES 84-98

The method described in Examples 5 to 9 and 80 to 83 is used to prepare the dyes described in the following table:

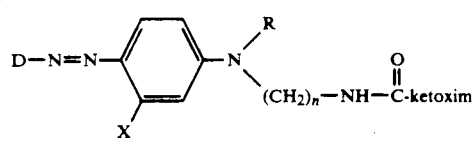

| Ex. | D | X | R | n | Oxime of | Colour | Melting point |
|---|---|---|---|---|---|---|---|
| 84 | -) | H | $C_2H_5$ | 2 | Acetophenone | red | 148-9° |

-continued

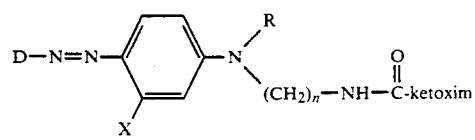

| Ex. | D | X | R | n | Oxime of | Colour | Melting point |
|---|---|---|---|---|---|---|---|
| 85 | 3-Cl, 4-O$_2$N-phenyl | H | C$_2$H$_5$ | 2 | H$_3$C, CH$_3$ / CH$_3$ cyclohexenone | red | 130–4 (90° sint) |
| 86 | 3-Cl, 4-O$_2$N-phenyl | H | C$_8$H$_{17}$ | 2 | Acetone | red | 107–8° |
| 87 | 3-Cl, 4-O$_2$N-phenyl | H | C$_4$H$_9$ | 2 | Cyclohexanone | red | 131–2° |
| 88 | 3-Cl, 4-O$_2$N-phenyl | H | C$_4$H$_9$ | 2 | Methyl isobutyl ketone | red | amorphous |
| 89 | 3-Cl, 4-O$_2$N-phenyl | H | C$_4$H$_9$ | 2 | Acetone | red | 132–3° |
| 90 | 3-CF$_3$, 4-O$_2$N-phenyl | H | C$_2$H$_5$ | 3 | Acetone | red | 109–10° |
| 91 | 3-CF$_3$, 4-O$_2$N-phenyl | H | C$_2$H$_5$ | 2 | Acetone | red | 161–2° |
| 92 | 3-CN, 4-O$_2$N-phenyl | H | C$_2$H$_5$ | 3 | Acetone | ruby | 145–6° |
| 93 | 3-CN, 4-O$_2$N-phenyl | H | C$_2$H$_5$ | 2 | Acetone | ruby | 173–4° |
| 94 | 3-NO$_2$, 4-O$_2$N, 5-Br-phenyl | CH$_3$ | C$_2$H$_5$ | 2 | Acetone | violet | 125–8° (115 sint) |

-continued

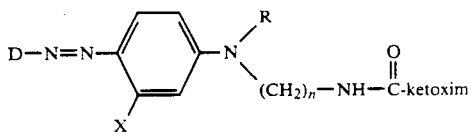

| Ex. | D | X | R | n | Oxime of | Colour | Melting point |
|-----|---|---|---|---|----------|--------|---------------|
| 95 | O₂N—⟨Cl-phenyl⟩— | NHCOCH₃ | C₂H₅ | 2 | Acetophenone | ruby | 189–189.5° |
| 96 | O₂N—⟨phenyl⟩— | NHCOCH₃ | C₂H₅ | 2 | Acetophenone | red | 139–141° |
| 97 | O₂N—⟨phenyl⟩— | NHCOCH₃ | C₂H₅ | 2 | Acetone | red | 135.5–136° |
| 98 | O₂N—⟨phenyl⟩— | NHCOCH₃ | C₂H₅ | 2 | Cyclohexanone | red | 148–149° |

EXAMPLE 99

86 g of the coupling component

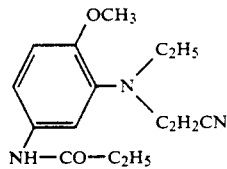

in 85% purity are hydrogenated at 70°–75° C. and 150 bar in 280 ml of ethanol and 87 g of liquid ammonia over 12.6 g of Raney nickel in the course of 5½ hours. The catalyst is filtered off and the hydrogenation solution is evaporated, leaving 85 g of a yellowish brown viscous mass. It is dissolved in about 500 ml of 1 N hydrochloric acid, and the solution is brought to pH 6.5–7 with sodium hydroxide and extracted with ethyl acetate to remove unconverted starting material.

The solution is then brought to pH 11.5 with sodium hydroxide and extracted with n-butanol. Washing, drying and evaporation of the butanol phases leaves 54 g of the aminopropyl compound of the formula

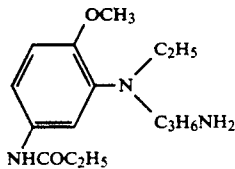

as a brown amorphous mass.

6.2 g (0.022 mol) thereof are dissolved in 20 ml of ethanol and added at 0°–5° C. to 200 ml of 1 N sulfuric acid. The diazonium salt solution prepared from 0.02 mol of 2-bromo-4,6-dinitroaniline is added dropwise at 0°–5° C. over 30 minutes while the pH is maintained between 2 and 3 by the addition of sodium hydroxide. The pH is then adjusted to 11.5, the mixture is filtered with suction, and the filter residue is washed and dried, leaving the amino dye of the formula

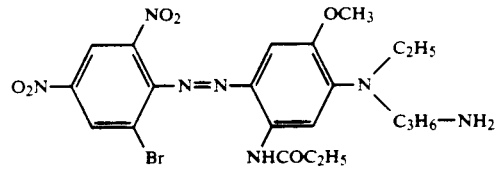

which melts at about 140° C.

It is reacted with excess chloroformic ester of acetoneoxime in dry pyridine to give the dye of the formula

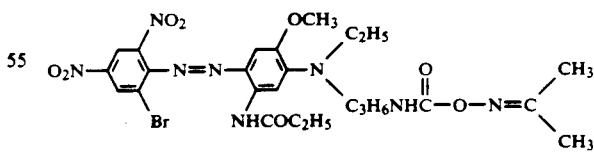

of melting point 100°–102° C.

This dye dyes polyester textile material in blue shades.

EXAMPLE 100

0.45 g of the bromodinitro dye of Example 99 is stirred in 15 ml of dimethylformamide together with 0.07 g of copper acetate monohydrate and 0.07 g of sodium nitrite at room temperature for 3 hours. The mixture is then diluted with plenty of water, and the precipitate is filtered off with suction, washed and dried, leaving 0.33 g of the dye of the formula

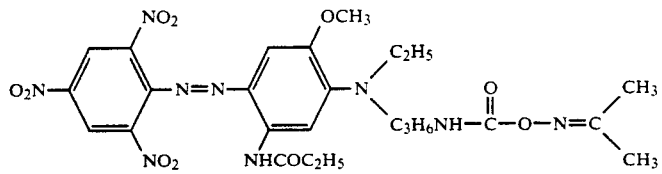

as a brown powder of melting point 150°-155° C. which dyes polyester textile material in greenish blue shades.

EXAMPLE 101

13 g of 3-ethylaminoacetanilide and 9.5 ml of chloroacetonitrile are stirred at 70°-80° C. with 7.5 g of sodium carbonate powder for 3 hours, the mixture is taken up in 80 ml of acetone, inorganic material is filtered off hot, water is added to the filtrate, and the precipitate is filtered off and dried, leaving 14.8 g of the cyanomethyl compound of the formula

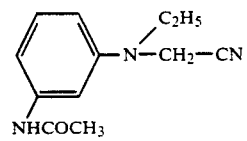

in the form of a pale brown powder of melting point 119°-120° C.

Hydrogenation in 100 ml of tetrahydrofuran using rhodium on aluminium oxide at 35° C. and 3 bar over 20 hours gives, following a conventional workup, 10.3 g of the coupling component of the formula

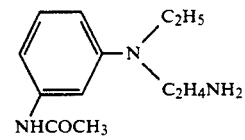

as a reddish brown amorphous mass. It is dissolved in 200 ml of glacial acetic acid and coupled to the diazonium salt solution of an equivalent amount of 2-bromo-4,6-dinitroaniline at 0°-10° C. at a pH maintained at 2 to 3. Filtering off with suction, suspending in water, liberating the base with sodium hydroxide solution, renewed filtering with suction, washing and drying gives 9.2 g of the dye of the formula

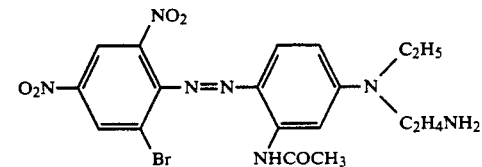

Reaction with the chloroformic ester of cyclohexanoneoxime and column chromatographic purfication over silica gel with ethyl acetate as eluent gives the dye of the formula

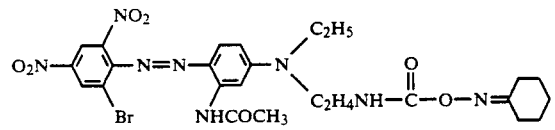

of melting point 98°-99° C. (94 sint.).

This dye dyes polyester textile material in violet shades.

EXAMPLE 102

11.3 g of anhydrous ε-caprolactam and 0.05 g of diazabicyclooctane are heated together to 80° C. 10.5 g of chloroethyl isocyanate are added dropwise to the melt with thorough stirring in the course of 30 minutes. The mixture is stirred at 80° C. for 7 hours. After cooling down to room temperature, the colourless melt is stirred for a further 3 hours under slightly reduced pressure. Standing overnight at 5° C. gives 21.4 g of colourless, slightly sticky crystals of the formula

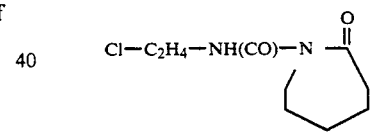

and of melting point 34°-37° C.

The crystals thus obtained are admixed with 10.9 g of N-ethylaniline, 0.8 g of potassium iodide and 10.6 g of sodium carbonate. The mixture is stirred at 100° C. overnight. 2 g of succinic anhydride are added, and the mixture is stirred at 80° C. for a further hour. Extraction with methylene chloride gives 24 g of the coupling component of the formula

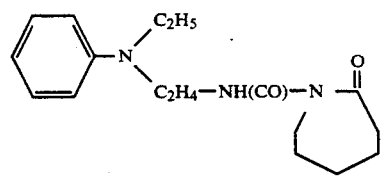

as a brown oil. However, the reaction mixture can also be taken up directly, without extraction, in 200 ml of 80% acetic acid and used for coupling in this form.

EXAMPLES 103-107

The method of Example 102 is also used to obtain the following coupling components:

| Example | | |
|---|---|---|
| 103 | 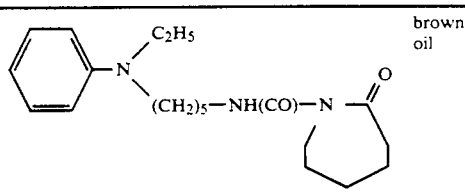 | brown oil |
| 104 | 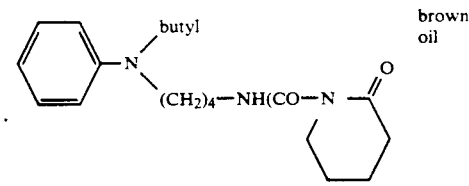 | brown oil |
| 105 | 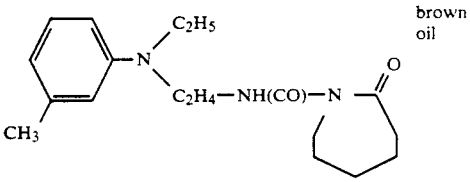 | brown oil |
| 106 | 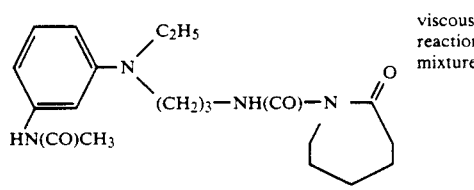 | viscous reaction mixture |
| 107 | 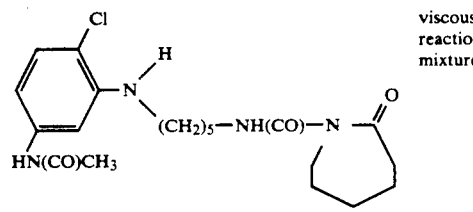 | viscous reaction mixture |

EXAMPLE 108

8.6 g of 2-chloro-4-nitroaniline are dissolved in 95 g of 7% nitrosylsulfuric acid, and the solution is stirred at room temperature for 2 hours. The solution is then poured onto a mixture of 200 g of ice and 2.5 g of urea. The yellowish diazonium salt solution is added dropwise at 0°–5° C. to a mixture of 15.2 g of coupling component of Example 102, 130 g of 80% acetic acid and 200 g of ice-water over 5 minutes. The mixture is brought to pH 3 by the addition of 30% sodium hydroxide solution and 600 g of ice at 0°–10° C. It is stirred for one hour and filtered, and the residue is washed and dried in air, leaving 23.2 g of a crude product. To purify the crude product, it is suspended in acetone. After 3 hour's stirring under reflux the suspension is stirred at room temperature overnight and then filtered. The filter residue comprises 15.3 g of blackish green crystals of the formula

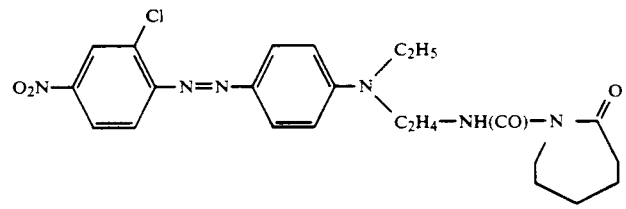

and of melting point 132°–134° C. The dye dyes polyester material in red shades.

EXAMPLE 109

0.11 g of caprolactam in 10 ml of toluene are stirred with 0.15 g of hexachlorodimethyl carbonate in the presence of 0.16 ml of N,N-diethylaniline under reflux for 4 hours. After cooling down to room temperature, the pale brown solution is admixed with 0.2 ml of triethylamine and 0.35 g of the aminoethyl dye described in Example 1, and the mixture is stirred at room temperature for 1 hour and then at 90° C. for another hour. The main component of the reaction mixture is the dye of the formula

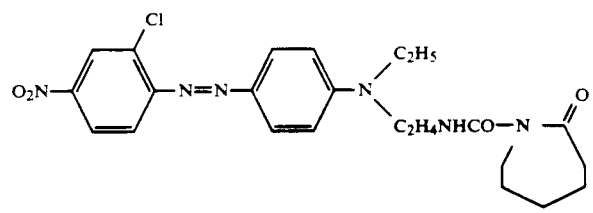

EXAMPLE 110

The method of Example 10 is used to formulate the dye of Example 108 as a 5 per cent aqueous dispersion. This dispersion is used to prepare a 0.5 per cent dye on weight of fibre HT dyeing on polyester.

If the dyed fabric is heated to 220° C. for 60 seconds before or after reduction clearing, the thermomigration fastness (test as described in Example 10) is found to be very good.

If the same dye dispersion is used to prepare a thermosol dyeing on polyester (10 g of dye/l, liquor pickup 50%, fixing temperature 220°), the result is likewise a very thermomigration-fast dyeing.

EXAMPLE 111

Example 102 is repeated, except that the ε-caprolactam is replaced by an equivalent amount of δ-valerolactam and the N-ethylaniline by an equivalent amount of N-methylaniline and right at the beginning an additional 20 ml of dimethylformamide are added as solvent. This gives the coupling component of the formula

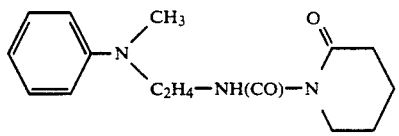

as a salt-containing solution in dimethylformamide.

Mixing half of this solution (0.05 mol) with 100 ml of 80% acetic acid and coupling it to 0.05 mol of diazotized 2-chloro-4-nitroaniline as described in Example 108 gives 15.5 g of a wine-red, oily product. Purification by column chromatography over silica gel with ethyl acetate gives a black powder of the formula

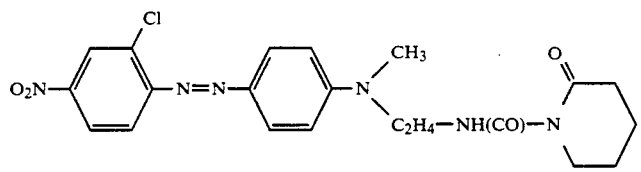

and of melting point 166°–169° C. The dye dyes polyester material in red shades.

EXAMPLE 112

Example 108 is repeated, except that the chloronitroaniline is replaced by an equivalent amount of 2-cyano-4-nitroaniline. This gives 7.7 g of a crude product. To purify the crude product, it is added to 50 ml of tertiary-butyl methyl ether, and the mixture is stirred under reflux for 3 hours. After cooling down to room temperature, the mixture is filtered and the filter residue is dried, giving 7.0 g of blackish brown crystals of the formula

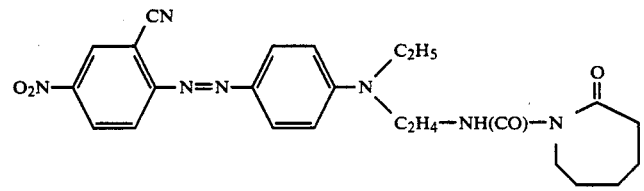

and of melting point 137°–139° C. The dye dyes polyester material in ruby shades.

EXAMPLE 113

Example 102 is repeated reacting 9.6 g of bromopentyl isocyanate first with 5.7 g of ε-caprolactam and then with 7.2 g of 3-(N-ethyl)aminoacetanilide to give the intermediate of the formula

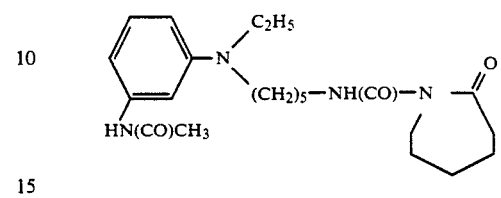

which is used without further purification.

10.5 g of 6-bromo-2,4-dinitroaniline are conventionally diazotized in sulfuric acid and coupled at 0°–10° C. onto a solution of the above-described coupling component in 200 ml of 50% acetic acid. The reaction mixture is admixed with 600 g of ice-water and stirred for several hours. The aqueous phase is then decanted off and 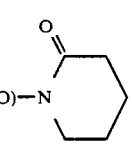 discarded. This washing operation is repeated two more times. Drying in air leaves 21.8 g of the product of the formula

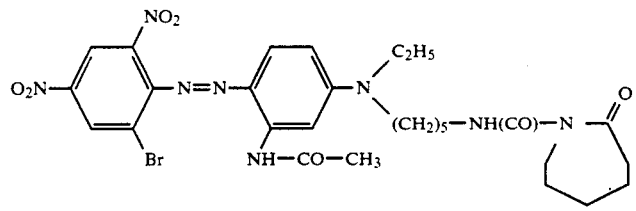

and of melting point 80°–85° C. The dye dyes polyester material in reddish blue shades.

EXAMPLE 114

16.9 g of the dye described in Example 113, 110 ml of dimethylformamide and 3.3 g of copper(I) cyanide are added together, and the mixture is stirred at 50° C. for 12 hours. The reaction mixture is then poured onto a mixture of 600 ml of ice-water and 13 g (0.03 mol) of iron(III) chloride. After 2 hour's stirring, the mixture is filtered, the filter residue is washed and dried leaving 10.4 g of a crude product. To purify the crude product, it is suspended in 150 ml of methanol, and the suspension is stirred under reflux for 3 hours. Cooling down to 0°–5° C., filtering and drying in air gives black crystals of the formula

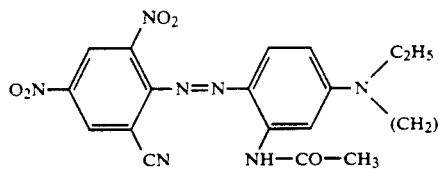

and of melting point 120°–125° C. The dye dyes polyester material in blue shades.

EXAMPLE 115

16.2 g of the coupling component obtained as described in Example 102 are dissolved in 20 ml of dimethylformamide, and 5.8 g of tetracyanoethylene are added. The mixture is stirred at 40° C. overnight. After cooling down to 0°–5° C., 180 ml of 70% methanol are added dropwise. After 2 hours' stirring at 0°–5° C., the mixture is filtered, the filter residue is washed and suspended in 50 ml of methanol, and the suspension is stirred under reflux for 2 hours. Cooling down, stirring at 0°–5° C. for 4 hours, filtering, washing and drying at 40° C. gives 7.5 g of black crystals of the formula

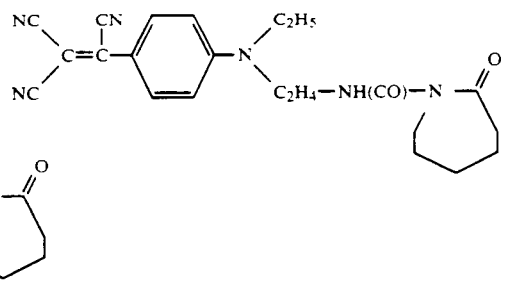

and of melting point 112°–115° C. The dye dyes polyester material in red shades.

EXAMPLES 116–120

The method of Example 115 is employed to obtain the following tricyanovinyl dyes:

| Example | Dye | Shade on polyester |
|---|---|---|
| 116 | NC\C=C/CN with phenyl-N(C2H5)(CH2)2—NH(CO)—N-caprolactam, CH3 on ring | ruby |
| 117 | NC\C=C/CN with phenyl-N(butyl)(CH2)5—NH(CO)—N-caprolactam | red |
| 118 | NC\C=C/CN with phenyl-N(CH3)C2H4—NH(CO)—O—N=C(CH3)2 | red |
| 119 | NC\C=C/CN with phenyl-N(C2H5)C2H4—NH(CO)—O—N=C(cyclohexyl), CH3 on ring | ruby |
| 120 | NC\C=C/CN with phenyl-N(C2H4CN)(CH2)3—NH(CO)—N-caprolactam | red |

EXAMPLE 121

0.8 g of the addition compound formed from chloroethyl isocyanate and ε-caprolactam described in Example 102, 10 ml of dimethylformamide, 1.1 g of the sodium salt of 1,4-diamino-3-cyano-2-tetrazolylanthraquinone and 0.1 g of potassium iodide are stirred at 80° C. overnight. 50 ml of methanol are added dropwise at 0°–5° C. After a further 2 hours' stirring at 0°–5° C., the mixture is filtered. The filter residue is washed with cold methanol and with water and is suspended in 20 ml of methanol, and the suspension is stirred under reflux for 2 hours. Cooling down, filtering off, washing and drying at 40° C. gives 0.8 g of blue powder of the formula

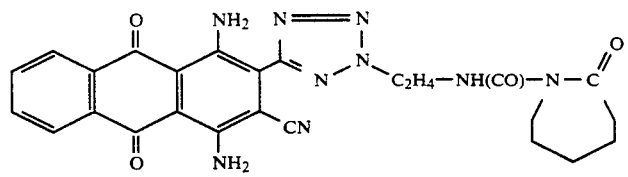

and of melting point 123°–133° C. The dyes dyes polyester material in blue shades.

EXAMPLES 122–132

The method described in Example 121 or in Example 83 is used to obtain the following anthraquinone dyes:

| Example | Dye | Shade on polyester |
|---|---|---|
| 122 | | blue |
| 123 | | blue |
| 124 | | violet |
| 125 | | violet |
| 126 | | violet |

-continued

| Example | Dye | Shade on polyester |
|---|---|---|
| 127 | anthraquinone with NH$_2$ groups, tetrazole linker -N=N-N(C$_2$H$_4$-NH(CO)-O-N=C(CH$_3$)$_2$), CN substituent | blue |
| 128 | 1-amino-4-hydroxyanthraquinone with -S-C$_2$H$_4$-NH(CO)-O-N=C(CH$_3$)$_2$ | violet |
| 129 | diaminoanthraquinone imide with N-C$_2$H$_4$-NH(CO)-O-N=C(CH$_3$)$_2$ | blue |
| 130 | diaminoanthraquinone imide with N-(CH$_2$)$_3$-NH(CO)-O-N=cyclohexylidene | blue |
| 131 | diaminoanthraquinone imide with N-C$_2$H$_4$-NH(CO)-N-caprolactam | blue |
| 132 | diaminoanthraquinone imide with N-(CH$_2$)$_3$-NH(CO)-N-caprolactam | blue |

EXAMPLES 133–200

The method described in Examples 1–5, 80–82, 99–101, 108–109 and 111–114 is used to prepare the dyes listed in the following table:

| Ex. | D | $X_1$ | $Y_1$ | $B_1$ | V | $R_5$ | Shade on polyester |
|---|---|---|---|---|---|---|---|
| 133 | H₃C—[thiophene with COOCH₃ and H₃COOC substituents]—S | —NH—C(=O)—CH₃ | H | —(CH₂)₃— | —O—N=C(CH₃)₂ | C₂H₅ | reddish violet |
| 134 | [benzothiazole with 5,6 + 6,7 dichloro] | H | H | —(CH₂)₃— | —O—N=C(CH₃)₂ | C₂H₅ | red |
| 135 | [benzothiazole with 5,6 + 6,7 dichloro] | H | H | —(CH₂)₃— | N-piperidone (1-substituted 2-oxopiperidine) | C₂H₅ | red |
| 136 | [benzothiazole with 5,6 + 6,7 dichloro] | H | H | —(CH₂)₃— | —O—N=cyclohexylidene | C₂H₅ | red |
| 137 | [benzothiazole with 5,6 + 6,7 dichloro] | H | H | —(CH₂)₃— | —O—N=C(CH₃)—CH₂—CH(CH₃)₂ | C₂H₅ | red |
| 138 | [benzothiazole with 5,6 + 6,7 dichloro] | H | H | —(CH₂)₅— | N-piperidone (1-substituted 2-oxopiperidine) | C₂H₅ | red |

-continued

| Ex. | D | $X_1$ | $Y_1$ | $B_1$ | V | $R_5$ | Shade on polyester |
|---|---|---|---|---|---|---|---|
| 139 | benzothiazole (5,6 + 6,7-dichloro) | $CH_3$ | H | $-(CH_2)_2-$ | caprolactam | $C_2H_5$ | ruby |
| 140 | benzothiazole (5,6 + 6,7-dichloro) | $CH_3$ | H | $-(CH_2)_2-$ | valerolactam | $C_2H_5$ | ruby |
| 141 | benzothiazole (5,6 + 6,7-dichloro) | $CH_3$ | H | $-(CH_2)_3-$ | $-O-N=C(CH_3)_2$ | $C_2H_5$ | ruby |
| 142 | $H_4C_2-S$-thiadiazole | $-NHCOCH_3$ | H | $-(CH_2)_3-$ | $-O-N=C(CH_3)_2$ | $C_2H_5$ | red |
| 143 | $H_5C_2-S$-thiadiazole | $-NHCOCH_3$ | H | $-(CH_2)_3-$ | cyclohexanone oxime | $C_2H_5$ | red |
| 144 | $H_5C_2-S$-thiadiazole | $-NHCOC_2H_5$ | H | $-(CH_2)_3-$ | Caprolactam | $C_2H_5$ | red |
| 145 | $H_5C_2-S$-thiadiazole | $-NHCOC_2H_5$ | H | $-(CH_2)_3-$ | Valerolactam | $CH_3$ | red |

-continued

| Ex. | D | $X_1$ | $Y_1$ | $B_1$ | V | $R_5$ | Shade on polyester |
|---|---|---|---|---|---|---|---|
| 146 | ![structure: H5C2-S-C(=N-N=)]  | —NHCOC$_2$H$_5$ | H | —(CH$_2$)$_3$— | Enantholactam | n-propyl | red |
| 147 | ![structure: H5C2-S-C(=N-N=)] | —NHCOC$_2$H$_5$ | H | —(CH$_2$)$_3$— | Caprylolactam | n-butyl | red |
| 148 | ![pyrrole with NC, NC, CH$_2$—CN, CH$_3$] | CH$_3$ | H | —(CH$_2$)$_3$— | —O—N=C(CH$_3$)(CH$_3$) | n-butyl | red |
| 149 | ![pyrrole with NC, NC, CH$_2$—CN, CH$_3$] | CH$_3$ | H | —(CH$_2$)$_3$— | Caprolactam | n-butyl | red |
| 150 | ![pyrrole with NC, NC, CH$_2$—CN, CH$_3$] | CH$_3$ | H | —(CH$_2$)$_3$— | Valerolactam | n-butyl | red |
| 151 | ![benzene with Br, Br, CH$_3$, H$_3$C] | —NHCOCH$_3$ | H | —(CH$_2$)$_3$— | Caprolactam | C$_2$H$_5$ | yellow |
| 152 | ![benzene with CN, CN, CH$_3$, H$_3$C] | —NHCOCH$_3$ | H | —(CH$_2$)$_3$— | Caprolactam | C$_2$H$_5$ | red |

-continued

| Ex. | D | $X_1$ | $Y_1$ | $B_1$ | V | $R_5$ | Shade on polyester |
|---|---|---|---|---|---|---|---|
| 153 | 3-CN, 5-CN, 4-CH$_3$ phenyl (with H$_3$C) | —NH—SO$_2$CH$_3$ | H | —(CH$_2$)$_3$— | —O—N=C(CH$_3$)$_2$ | n-butyl | red |
| 154 | 3-CN, 5-CN, 4-CH$_3$, (O$_2$N) phenyl | —CH$_3$ | H | —(CH$_2$)$_3$— | —O—N=C(CH$_3$)$_2$ | C$_2$H$_5$ | reddish blue |
| 155 | 3-CN, 5-CN, 4-CH$_3$, (O$_2$N) phenyl | —CH$_3$ | H | —(CH$_2$)$_3$— | Caprolactam | C$_2$H$_5$ | reddish blue |
| 156 | 3-NO$_2$, 5-Cl, 4-CH$_3$, (O$_2$N) phenyl | —CH$_3$ | —OCH$_3$ | —(CH$_2$)$_3$— | —O—N=C(CH$_3$)$_2$ | C$_2$H$_5$ | blue |
| 157 | 3-NO$_2$, 5-Cl, 4-CH$_3$, (O$_2$N) phenyl | —CH$_3$ | —OCH$_3$ | —(CH$_2$)$_3$— | Caprolactam | C$_2$H$_5$ | blue |

-continued

| Ex. | D | $X_1$ | $Y_1$ | $B_1$ | V | $R_5$ | Shade on polyester |
|---|---|---|---|---|---|---|---|
| 158 | 2,4,6-trinitrophenyl (NO2, NO2, O2N) | —NHCOCH3 | H | —(CH2)3— | Caprolactam | $C_2H_5$ | blue |
| 159 | 2,4,6-trinitrophenyl | —NHCOCH3 | —OCH3 | —(CH2)3— | $-O-N=C(C_2H_5)(CH_3)$ | $C_2H_5$ | greenish blue |
| 160 | 2,4-dinitro-6-cyanophenyl | —NHCOCH3 | H | —(CH2)3— | piperidinyl N-oxide (—O—N=cyclohexyl) | $C_2H_5$ | blue |
| 161 | 2,4-dinitro-6-cyanophenyl | —NHCOCH3 | —OCH3 | —(CH2)3— | Caprolactam | $C_2H_5$ | greenish blue |
| 162 | 2-cyano-4-nitro-6-bromophenyl | —NHCOCH3 | H | —(CH2)3— | Caprolactam | $C_2H_5$ | reddish blue |

-continued

| Ex. | D | $X_1$ | $Y_1$ | $B_1$ | V | $R_5$ | Shade on polyester |
|---|---|---|---|---|---|---|---|
| 163 | 3-CN, 5-Cl, 4-$O_2N$-phenyl (2-methyl) | $-NH-COC_2H_5$ | H | $-(CH_2)_3-$ | $-O-N=C(CH_3)(CH_3)$ | $C_2H_5$ | reddish blue |
| 164 | 2-CN, 4-$O_2N$-phenyl (methyl) | $-NH-COC_2H_5$ | H | $-(CH_2)_3-$ | Enantholactam | $CH_3$ | ruby |
| 165 | 2-CN, 4-$O_2N$-phenyl (methyl) | $-NHCOCH_3$ | H | $-(CH_2)_2-$ | $-O-N=C(C_2H_5)(CH_3)$ | $C_2H_5$ | ruby |
| 166 | 2-Cl, 6-Cl, 4-$O_2N$-phenyl (methyl) | Cl | H | $-(CH_2)_3-$ | Caprolactam | $C_2H_5$ | yellowish brown |
| 167 | 2-$SO_2CH_3$, 4-$O_2N$-phenyl (methyl) | H | H | $-(CH_2)_3-$ | Caprolactam | $C_2H_5$ | ruby |
| 168 | $NO_2$, $O_2N$-thiazole (methyl) | $-NHCOCH_3$ | H | $-(CH_2)_3-$ | Caprolactam | $C_2H_5$ | green |
| 169 | $NO_2$, $CH_3CO$-thiophene (methyl) | $-NHCOCH_3$ | H | $-(CH_2)_3-$ | Caprolactam | $C_2H_5$ | blue |

-continued

| Ex. | D | $X_1$ | $Y_1$ | $B_1$ | V | $R_5$ | Shade on polyester |
|---|---|---|---|---|---|---|---|
| 170 | 3-CN, 5-CF$_3$, 4-O$_2$N-phenyl | —NHCOCH$_3$ | OCH$_3$ | —(CH$_2$)$_3$— | Acetoneoxime | C$_2$H$_5$ | blue |
| 171 | 3-CN, 5-CF$_3$, 4-O$_2$N-phenyl | —NHCOCH$_3$ | OCH$_3$ | —(CH$_2$)$_3$— | Caprolactam | C$_2$H$_5$ | blue |
| 172 | 3-Cl, 4-O$_2$N-phenyl | H | H | —(CH$_2$)$_5$— | Caprolactam | C$_2$H$_5$ | red |
| 173 | 3-Cl, 4-O$_2$N-phenyl | H | H | —(CH$_2$)$_4$— | Enantholactam | C$_2$H$_5$ | red |
| 174 | 3-Cl, 4-O$_2$N-phenyl | H | H | —(CH$_2$)$_4$— | Cyclohexanoneoxime | C$_2$H$_5$ | red |
| 175 | 3-NO$_2$, 4-O$_2$N-phenyl | H | H | —(CH$_2$)$_4$— | Valerolactam | C$_2$H$_5$ | ruby |

-continued

| Ex. | D | $X_1$ | $Y_1$ | $B_1$ | V | $R_5$ | Shade on polyester |
|---|---|---|---|---|---|---|---|
| 176 | benzisothiazole with $O_2N$ | H | H | $-(CH_2)_4-$ | Caprolactam | $C_2H_5$ | red |
| 177 | benzisothiazole with $H_3CSO_2$ | H | H | $-(CH_2)_2-$ | Valerolactam | $C_2H_5$ | red |
| 178 | benzisothiazole with $CF_3$ | $CH_3$ | H | $-(CH_2)_2-$ | Caprolactam | $C_2H_5$ | red |
| 179 | phthalimide with $H_5C_2-$ | $-NHCOCH_3$ | H | $-(CH_2)_3-$ | Caprolactam | $C_2H_5$ | red |
| 180 | phenyl with CN and $O_2N$ | $-NHCOCH_3$ | H | $-(CH_2)_5-$ | Caprolactam | $C_2H_5$ | violet |
| 181 | benzisothiazole with Br, Br | $CH_3$ | H | $-(CH_2)_2-$ | Valerolactam | $C_2H_5$ | red |
| 182 | phenyl with Cl and $O_2N$ | $-NHCOCH_3$ | H | $-(CH_2)_3-$ | Caprolactam | $-C_2H_4CN$ | red |

-continued

| Ex. | D | $X_1$ | $Y_1$ | $B_1$ | V | $R_5$ | Shade on polyester |
|---|---|---|---|---|---|---|---|
| 183 | 3,5-dibromo-4-methylphenyl (Br, Br, CH₃) | H | H | $-(CH_2)_2-$ | Caprolactam | $CH_3$ | yellow |
| 184 | 3,5-dicyano-4-methylphenyl (CN, CN, CH₃) | H | H | $-(CH_2)_2-$ | Caprolactam | $CH_3$ | red |
| 185 | thiadiazole with $H_5C_2S$ and isopropyl | H | H | $-(CH_2)_2-$ | Caprolactam | $CH_3$ | red |
| 186 | 3-chloro-4-nitrophenyl (Cl, $O_2N$) | H | H | $-(CH_2)_2-$ | Valerolactam | $CH_3$ | red |
| 187 | 3-chloro-4-nitrophenyl (Cl, $O_2N$) | H | H | $-(CH_2)_2-$ | Cyclohexanoneoxime | $CH_3$ | red |
| 188 | 4-nitrophenyl ($O_2N$) | H | H | $-(CH_2)_2-$ | $-N-C(=O)-(CH_2)_6-$ | $-C_2H_5$ | scarlet |
| 189 | 4-nitrophenyl ($O_2N$) | H | H | $-(CH_2)_2-$ | $-N-C(=O)-(CH_2)_7-$ | $-C_2H_5$ | scarlet |

-continued

| Ex. | D | $X_1$ | $Y_1$ | $B_1$ | V | $R_5$ | Shade on polyester |
|---|---|---|---|---|---|---|---|
| 190 | 4-CH₃, 3-CN, 6-O₂N phenyl | H | H | $-(CH_2)_2-$ | $\beta$-lactam ring with $(CH_2)_7$ | $-C_2H_5$ | ruby |
| 191 | 4-CH₃, 3-CN, 6-O₂N phenyl | H | H | $-(CH_2)_2-$ | $\beta$-lactam ring with $(CH_2)_6$ | $-C_2H_5$ | ruby |
| 192 | 3-CH₃, 4-CN isothiazole | $-NHCOCH_3$ | H | $-(CH_2)_4-$ | N-methyl caprolactam | $-C_2H_5$ | bluish red |
| 193 | 3-CH₃, 4-CN isothiazole | $-NHCOCH_3$ | H | $-(CH_2)_3-$ | $-O-N=C(CH_3)(C_2H_5)$ | $-C_2H_5$ | bluish red |
| 194 | 5-O₂N benzisothiazole | H | H | $-(CH_2)_2-$ | N-methyl caprolactam | $-C_2H_5$ | blue |
| 195 | 5-O₂N benzisothiazole | $-NHC(=O)CH_3$ | H | $-(CH_2)_5-$ | N-methyl caprolactam | $-C_2H_5$ | greenish blue |

-continued

| Ex. | D | $X_1$ | $Y_1$ | $B_1$ | V | $R_5$ | Shade on polyester |
|---|---|---|---|---|---|---|---|
| 196 | 3-Cl-4-(O$_2$N)-phenyl | H | H | $-(CH_2)_3-$ | N-methyl caprolactam | $-C_2H_4CN$ | red |
| 197 | 3-Cl-4-(O$_2$N)-phenyl | $-NH-C(=O)-CH_3$ | Cl | $-(CH_2)_5-$ | N-methyl caprolactam | H | red |
| 198 | 3-Cl-4-(O$_2$N)-phenyl | H | H | $-C_2H_4-$ | cyclohexanone oxime | $-C_2H_4CN$ | red |
| 199 | 3,5-dibromobenzisothiazolyl | $-NH-C(=O)-CH_3$ | H | $-(CH_2)_3-$ | N-methyl caprolactam | $-C_2H_5$ | blue |
| 200 | benzisothiazolyl | $-NH-C(=O)-CH_3$ | H | $-(CH_2)_3-$ | N-methyl caprolactam | $-C_2H_5$ | blue |

What is claimed is:
1. A disperse dye of the formula

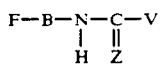 (1)

where
F is the radical of a dye which is free of water-solubilizing groups, selected from the group consisting of nitro dyes, nitrodiphenylamine dyes, quinoline dyes, aminonaphthoquinone dyes, coumarin dyes, methine dyes, anthraquinone dyes, tricyanovinyl dyes and azo dyes,
B is a direct bond or a bridge member selected from the group consisting of straight-chain or branched alkylene of 2 to 8 carbon atoms or one of the following groups:

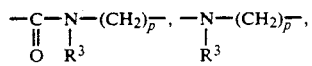

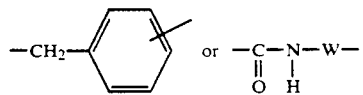

where $R^3$ is hydrogen or $C_1$-$C_6$alkyl, p is an integer from 1 to 8 and W is a divalent organic radical selected from the group consisting of straight-chain or branched alkylene of 2 to 8 carbon atoms, unsubstituted or $C_1$-$C_4$alkyl-substituted phenylene, $C_1$-$C_4$alkylene-phenylene-$C_1$-$C_4$-alkylene, phenylene-$C_1$-$C_4$-alkylene-phenylene or a radical of the formula

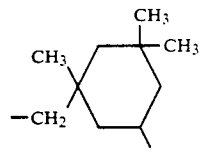

Z is O or S and
V is the radical of a group H—V, where H—V is an oxime of the formula

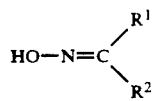 (2)

or a lactam of the formula

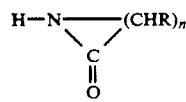 (3)

in which $R^1$ and $R^2$ are each independently of the other
a) unsubstituted $C_1$-$C_{12}$alkyl or $C_1$-$C_{12}$alkyl which is substituted by hydroxy, $C_1$-$C_4$alkoxy, halogen, cyano, phenyl, —CO—U or —O—CO—U, where U is $C_1$-$C_6$alkyl or phenyl or
b) phenyl, naphthyl or pyridyl or phenyl which is substituted by $C_1$-$C_4$alkyl, $C_1$-$C_4$alkoxy, bromine, chlorine, nitro or $C_1$-$C_4$alkylcarbonylamino, or $R^1$ and $R^2$ together with the carbon atom linking them form a cyclopentyl, cyclohexyl, methylcyclohexyl or cycloheptyl ring,
R is hydrogen or $C_1$-$C_4$alkyl and
n is an integer from 4 to 11.

2. A dispersed dye according to claim 1, wherein Z is oxygen.

3. A disperse dye according to claim 1, wherein $R^1$ and $R^2$ are each independently of the other $C_1$-$C_{12}$alkyl, phenyl, naphthyl or pyridyl or $R^1$ and $R^2$ together with the carbon atom linking them are cyclopentyl, cyclohexyl or cycloheptyl.

4. A disperse dye according to claim 1, wherein R is methyl or hydrogen and n is 4, 5 or 6.

5. A disperse dye of the formula

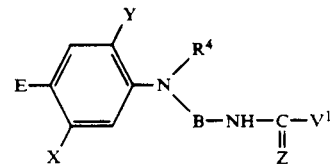 (4)

where
E is D—N=N— or

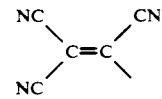

wherein D is the radical of a carbocyclic or heterocyclic diazo component selected from the group consisting of thienyl, phenylazothienyl, thiazolyl, isothiazolyl, 1,2,4-thiadiazolyl, 1,3,4-thiadiazolyl, benzothiazolyl, benzisothiazolyl, pyrazolyl, 1,2,3-triazolyl, 1,2,4-triazolyl and imidazolyl, or phenyl, each of these groups being unsubstituted or substituted by alkyl, alkoxy or alkylthio each of 1 to 4 carbon atoms, phenyl, halogen, trifluoromethyl, cyano, nitro, acetyl or benzoyl, carbo-$C_1$-$C_4$alkoxy, alkyl sulfone of 1 to 4 carbon atoms, phenyl sulfone, phenoxysulfonyl, sulfonamido or phenylazo, or where 2 adjacent substituents on the ring systems mentioned form further fused-on phenyl rings or cyclic imides,
X is hydrogen, $C_1$-$C_4$alkyl, $C_1$-$C_4$alkoxy, halogen, $C_1$-$C_4$alkylsulfonylamino or a group of the formula —NH—CO—NHQ, in which Q is hydrogen, $C_1$-$C_4$alkyl or phenyl, or X is a group of the formula

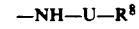 (5)

where U is —CO— or —$SO_2$— and $R^8$ is
a) unsubstituted $C_1$-$C_{12}$alkyl or $C_1$-$C_{12}$alkyl which is substituted by hydroxyl, $C_1$-$C_4$alkoxy, halogen, cyano, phenyl, —CO—U or —O—CO—U, where U is $C_1$-$C_6$alkyl or phenyl or
b) phenyl or phenyl which is substituted by $C_1$-$C_4$alkyl, $C_1$-$C_4$alkoxy, bromine, chlorine, nitro or $C_1$-$C_4$alkylcarbonylamino,
Y is hydrogen, halogen, $C_1$-$C_4$alkyl, $C_1$-$C_4$alkoxy, $C_1$-$C_4$alkoxy-$C_1$-$C_4$alkyl or $C_1$-$C_4$alkoxy-$C_2$-$C_4$alkoxy,
$R^4$ is $C_1$-$C_{12}$alkyl, $C_2$-$C_6$alkenyl or phenyl, or Y and $R^4$ together with the nitrogen atom and the two carbon atoms linking them form a 5- or 6-membered ring, B is a radical of the formula

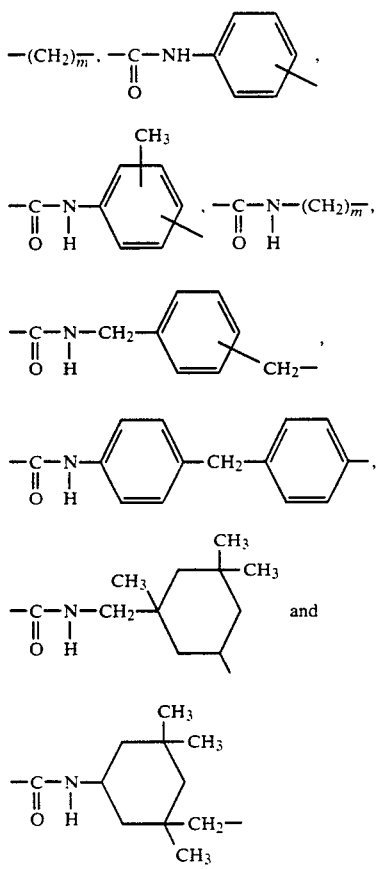

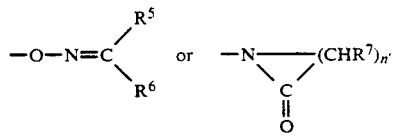

where m is an integer from 2 to 6,
Z is O or S and
$V^1$ is

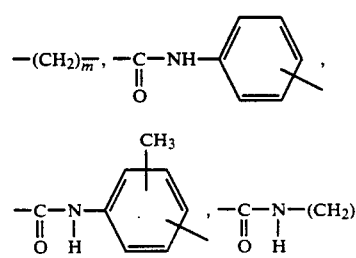

where $R^5$ and $R^6$ are each independently of the other $C_1$-$C_6$alkyl or $R^5$ and
$R^6$ together with carbon atom linking them form a cyclopentyl, cyclohexyl or cycloheptyl radical,
$R^7$ is methyl or hydrogen and
n' is 4, 5, 6 or 7.

6. A disperse dye according to claim 5, wherein E is D—N=N—.

7. A disperse dye according to claim 5, wherein D is a benzothiazolyl or benzisothiazolyl radical which is unsubstituted or monosubstituted or disubstituted by bromine, nitro or chlorine or is a phenyl radical which is monosubstituted or disubstituted by nitro, chlorine, cyano, methylsulfonyl or ethylsulfonyl or phenylazo.

8. A disperse dye according to claim 5, wherein X is hydrogen, methyl, methoxy, chlorine, bromine, acetylamino or ureido.

9. A disperse dye according to claim 5, wherein Y is chlorine, methyl, methoxy, methoxyethyl, methoxyethoxy or hydrogen.

10. A disperse dye of the formulae

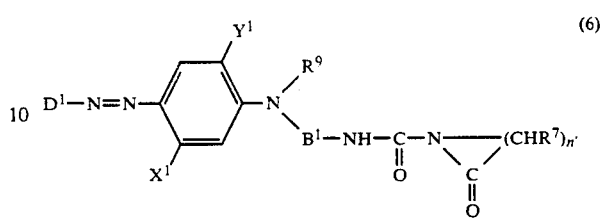

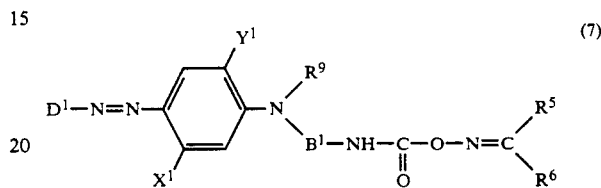

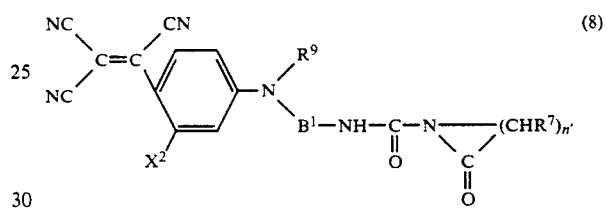

or

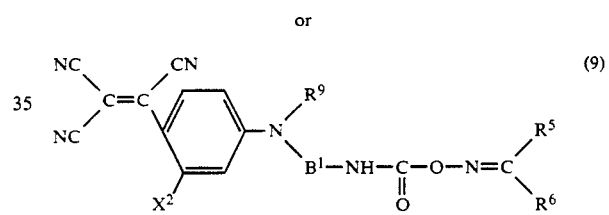

where
$D^1$ is a benzothiazolyl radical which is unsubstituted or monosubstituted or disubstituted by chlorine, or is a phenyl radical which is monosubstituted or disubstituted by nitro, chlorine, cyano, methylsulfonyl, ethylsulfonyl or phenylazo,
$X^1$ is hydrogen, methyl, methoxy, chlorine, bromine or acetylamino,
$Y^1$ is chlorine, methyl, methoxy, methoxyethyl, methoxyethoxy or hydrogen,
$X^2$ is hydrogen, methyl, methoxy, chlorine or bromine,
$R^9$ is $C_1$-$C_4$alkyl which is unsubstituted or substituted by hydroxyl, cyano, $C_1$-$C_4$alkoxy or phenyl,
$B^1$ is a radical of the formula -continued

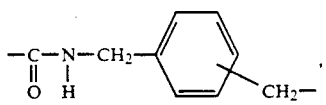

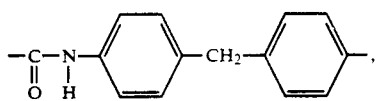

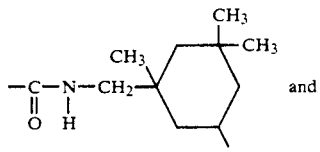 and

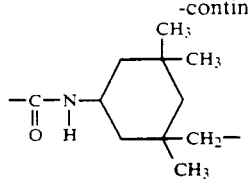

where m is an integer from 2 to 6,
R⁵ and R⁶ are each independently of the other $C_1$-$C_6$alkyl or $R^5$ and $R^6$ together with the carbon atom linking them form a cyclopentyl, cyclohexyl or cycloheptyl radical,
$R^7$ is methyl or hydrogen, and
n' is 4, 5, 6 or 7.

11. A process for preparing a dye of the formula (4) according to claim 5 in which $V^1$ is an oxime radical, which comprises reacting a compound of the formula

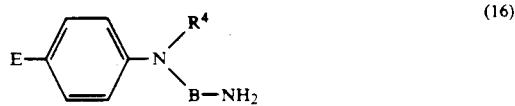

(16)

with a haloformic ester of an oxime of the formula

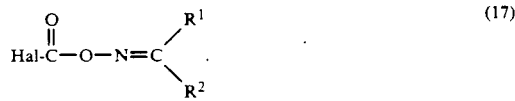

(17)

* * * * *